United States Patent
Börjesson et al.

(10) Patent No.: US 9,446,102 B2
(45) Date of Patent: Sep. 20, 2016

(54) POLYPEPTIDES HAVING ALPHA-GLUCURONIDASE ACTIVITY AND POLYNUCLEOTIDES ENCODING SAME

(71) Applicant: Novoyzmes A/S, Bagsvaerd (DK)

(72) Inventors: Johan Börjesson, Malmo (SE); Anders Vikso-Nielsen, Slangerup (DK); Nikolaj Spodsberg, Bagsvaerd (DK); Kristian Krogh, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/395,960

(22) PCT Filed: Apr. 22, 2013

(86) PCT No.: PCT/EP2013/058293
§ 371 (c)(1),
(2) Date: Oct. 21, 2014

(87) PCT Pub. No.: WO2013/160248
PCT Pub. Date: Oct. 31, 2013

(65) Prior Publication Data
US 2015/0110765 A1    Apr. 23, 2015

Related U.S. Application Data

(60) Provisional application No. 61/638,712, filed on Apr. 26, 2012.

(30) Foreign Application Priority Data

Apr. 23, 2012 (EP) .................................... 12165163

(51) Int. Cl.
| | |
|---|---|
| *C12N 9/44* | (2006.01) |
| *A61K 38/47* | (2006.01) |
| *C07H 21/04* | (2006.01) |
| *C12N 15/82* | (2006.01) |
| *C12N 9/24* | (2006.01) |
| *A61K 38/46* | (2006.01) |

(52) U.S. Cl.
CPC ............. *A61K 38/47* (2013.01); *A61K 38/465* (2013.01); *C12N 9/2402* (2013.01); *C12N 9/2451* (2013.01); *C12N 15/8242* (2013.01); *C12N 15/8245* (2013.01); *C12N 15/8246* (2013.01); *C12N 15/8257* (2013.01); *C12Y 302/01139* (2013.01); *C12Y 301/01* (2013.01)

(58) Field of Classification Search
CPC ............... C12P 19/14; C12N 15/8245; C12N 15/8246; C12N 9/2451; C12Y 302/01139
USPC ................... 435/320.1, 252.2, 209; 536/23.2
See application file for complete search history.

(56) References Cited

U.S. PATENT DOCUMENTS

| | | | |
|---|---|---|---|
| 8,080,398 B2* | 12/2011 | Holm et al. .................. | 435/161 |
| 2009/0119022 A1 | 5/2009 | Timberlake et al. | |
| 2010/0273214 A1* | 10/2010 | Holm et al. ................. | 435/69.1 |

OTHER PUBLICATIONS

Spanikova et al, 2006, FEBS Lett 580 (19), 4597-4601.
Galagan et al, 2005, Nature 438(7071), 1105-1115.
Galagan et al, 2005—Uniprot Acces No. Q5AQZ4.
Bauer et al, 2006, Proc Natl Aca Sci103 (3), 11417-11422.

* cited by examiner

*Primary Examiner* — Younus Meah
(74) *Attorney, Agent, or Firm* — Robert Starnes

(57) ABSTRACT

The present invention relates to isolated polypeptides having alpha-glucuronidase activity, catalytic domains and polynucleotides encoding the polypeptides, catalytic domains. The invention also relates to nucleic acid constructs, vectors, and host cells comprising the polynucleotides as well as methods of producing and using the polypeptides or catalytic domains.

29 Claims, 3 Drawing Sheets

SEQUENCE LISTING

<160> NUMBER OF SEQ ID NOS: 14

<210> SEQ ID NO 1
<211> LENGTH: 2544
<212> TYPE: DNA
<213> ORGANISM: Emericella nidulans

<400> SEQUENCE: 1

```
atgcggagct tctgctgct gaccgcgcta ctgggcgtcg ccgccgtcgc tgaagatggg      60
ctggcagcct ggctgcggta tgcgcccatc cctcatgcga aatcgtacca caaaaatcta     120
ccgtcagtaa ttgtgccatt gaatgcaacg gctggacgac cgatagatac tgcagcttac     180
gagctcgtcg atggcattaa ggggatattt ggcaagcgag tcaccctcaa gaacgagacg     240
cgtgacgacc caaaccttcc cgccgtgacg gttggcactg tcgaagcata cgctgaagct     300
ggcggcgatg tgtccagtgt tccggaactc atcgacgacg ggtactatct cagcgtcgcg     360
gggcccagcg tcttaatcct cggccagaat gagcgcggag ccctgtacgg aaccttccag     420
tatctcgagc gactggcgca ggggaaggtc tcggatacct cgttcgcatc caacccgagc     480
gcgccgatac gatgggtaaa tcaatgggac aatctacagg acggcggcac ccacgggagc     540
gtggagaggg gatacggagg agactccatc ttcttctggg atggcagggt ccgcgacgat     600
ctcacgcgcg cgagccagta tgctcgtctg ctggcttcga tcggtctcaa tgctgtcatc     660
gtcaataatg tcaatgcgaa tgagacgatc ctgacgcagg agaacatgga tggcgtagcc     720
aggatagcgg atgctttccg tccgtacggc atccagctcg gtctatcttt gaactttgcg     780 tcccccccagt cactaggcgg cctggataca tttgatccat ttgacgagag agtcatcagc     840 tggtggggg aaatcaccga tgagctgtac gagaggatcc ccgacatggc aggctatctg     900
gttaaggcca actccgaagg ccagccgggc cccttttacct acaaccgaac gctggccgat     960
ggagccaacc tctttgcgcg gcattgcag cctcacggtg ggatcgtgct gttccgcgcg    1020
tttgtctacg accacgagaa tctcaacgag acgctcgact ggaaggctga ccgcgcaaac    1080
gcggcagtgg agttctttga cgggttggat ccccaattcg aggacaacgt cgtgattcag    1140
atcaagaatg ggccgatcga ttttcaggtc cgcgaacctg tctcgcccct attcgcccat    1200
ctatcgcaga cggccagtgc agtagagcta caggtcaccc aagagtatct cggacagcaa    1260
tgccatctgg tctatcttgc acctatgtgg aaagaagttc tcgattttga cctccgcgtt    1320
gacggcaaag actcggttgt cagtgatatc gtcagcggca ggcggttcaa caatactctc    1380
ggtggctacg cgggagtggt taatgttggc ctcaacacga cttggctagg aagtcacttg    1440
gccatgtcaa acctctacgc ttacggccgg ctcgcctggg acccgtcggc cgactcggtg    1500
gagctgttac aggagtggat caagatgaca ttcagtcacg atcaagaggt cgtcgacgtg    1560
atcacgaaga tgtcgatgga gtcttggccc gcgtacgaga actactctgg aaacctcggg    1620
```

```
atccagacgc tgactgacat tctgcttggc cattacggcc ccaacccagc atctcaggac    1680
ggcaaccoct ggggccagtg gacccgcgcg gacgccgaca gcatcgggat ggaccgcacc    1740
gtctggaacg gcaccggcaa tgcgggtcag tacccggagg aggtatatca gatgtacgaa    1800
aatatcgaca ccaccccoga caacctgctg ctgtggttcc accacgtgcc atacacccag    1860
cgcctcaaga gcggcaagac ggtgatccag cacttctacg acgcgcacta ccgcggcagc    1920
gcgactgccc agacatttgt ctcgctgtgg aagactatta agggcaagat cgacaaggag    1980
cgctatgagc atgtgctctt ccggctagtt tatcaagcag ccacgcgct ggtttggcgc     2040
gattccatca cgaacttcta ctacaacaag tctgggattc ccgatgaagc cggccgggtc    2100
ggcaaccatc cctatcgcat cgaggctgaa gacatggagc tggacgggta cgagccgtac    2160
ctggtcagcc cgtttgaggc agcaagcggc tcccactgca tcgtcacctc aaacaattcg    2220
acggaaggcc gggcctcgac gccgctgaag gtcaaaaatg gcaagtacga catcgcggtc    2280
aactattttg accaggcaat tggtaactca acctggaggc tgttccttga tgacgatctt    2340
gttggggagt ggaagggcga cttggaatat attttagggc gcgcaccgtc tccttacatt    2400
gatgggcaga cggccgcgcg gattacgttc aagcacgtcc atattaagtc gcgctccaca    2460
ctgagcattg taggcatccc ggatggaatg gagcctgcgc caattgacta cgtctcgatt    2520
ctgccagagg gtgttattga ctaa                                           2544

<210> SEQ ID NO 2
<211> LENGTH: 847
<212> TYPE: PRT
<213> ORGANISM: Emericella nidulans

<400> SEQUENCE: 2

Met Arg Ser Phe Leu Leu Leu Thr Ala Leu Leu Gly Val Ala Ala Val
1               5                   10                  15

Ala Glu Asp Gly Leu Ala Ala Trp Leu Arg Tyr Ala Pro Ile Pro His
            20                  25                  30

Ala Lys Ser Tyr His Lys Asn Leu Pro Ser Val Ile Val Pro Leu Asn
        35                  40                  45

Ala Thr Ala Gly Arg Pro Ile Asp Thr Ala Ala Tyr Glu Leu Val Asp
    50                  55                  60

Gly Ile Lys Gly Ile Phe Gly Lys Arg Val Thr Leu Lys Asn Glu Thr
65                  70                  75                  80

Arg Asp Asp Pro Asn Leu Pro Ala Val Thr Val Gly Thr Val Glu Ala
                85                  90                  95

Tyr Ala Glu Ala Gly Gly Asp Val Ser Ser Val Pro Glu Leu Ile Asp
            100                 105                 110

Asp Gly Tyr Tyr Leu Ser Val Ala Gly Pro Ser Val Leu Ile Leu Gly
        115                 120                 125

Gln Asn Glu Arg Gly Ala Leu Tyr Gly Thr Phe Gln Tyr Leu Glu Arg
    130                 135                 140

Leu Ala Gln Gly Lys Val Ser Asp Thr Ser Phe Ala Ser Asn Pro Ser
145                 150                 155                 160

Ala Pro Ile Arg Trp Val Asn Gln Trp Asp Asn Leu Gln Asp Gly Gly
                165                 170                 175

Thr His Gly Ser Val Glu Arg Gly Tyr Gly Gly Asp Ser Ile Phe Phe
            180                 185                 190

Trp Asp Gly Arg Val Arg Asp Asp Leu Thr Arg Ala Ser Gln Tyr Ala
        195                 200                 205
```

-continued

```
Arg Leu Leu Ala Ser Ile Gly Leu Asn Ala Val Ile Val Asn Asn Val
    210                 215                 220

Asn Ala Asn Glu Thr Ile Leu Thr Gln Glu Asn Met Asp Gly Val Ala
225                 230                 235                 240

Arg Ile Ala Asp Ala Phe Arg Pro Tyr Gly Ile Gln Leu Gly Leu Ser
                245                 250                 255

Leu Asn Phe Ala Ser Pro Gln Ser Leu Gly Gly Leu Asp Thr Phe Asp
                260                 265                 270

Pro Phe Asp Glu Arg Val Ile Ser Trp Trp Gly Glu Ile Thr Asp Glu
            275                 280                 285

Leu Tyr Glu Arg Ile Pro Asp Met Ala Gly Tyr Leu Val Lys Ala Asn
    290                 295                 300

Ser Glu Gly Gln Pro Gly Pro Phe Thr Tyr Asn Arg Thr Leu Ala Asp
305                 310                 315                 320

Gly Ala Asn Leu Phe Ala Arg Ala Leu Gln Pro His Gly Gly Ile Val
                325                 330                 335

Leu Phe Arg Ala Phe Val Tyr Asp His Glu Asn Leu Asn Glu Thr Leu
                340                 345                 350

Asp Trp Lys Ala Asp Arg Ala Asn Ala Ala Val Glu Phe Phe Asp Gly
            355                 360                 365

Leu Asp Pro Gln Phe Glu Asp Asn Val Val Ile Gln Ile Lys Asn Gly
    370                 375                 380

Pro Ile Asp Phe Gln Val Arg Glu Pro Val Ser Pro Leu Phe Ala His
385                 390                 395                 400

Leu Ser Gln Thr Ala Ser Ala Val Glu Leu Gln Val Thr Gln Glu Tyr
                405                 410                 415

Leu Gly Gln Gln Cys His Leu Val Tyr Leu Ala Pro Met Trp Lys Glu
                420                 425                 430

Val Leu Asp Phe Asp Leu Arg Val Asp Gly Lys Asp Ser Val Val Ser
            435                 440                 445

Asp Ile Val Ser Gly Arg Arg Phe Asn Asn Thr Leu Gly Gly Tyr Ala
    450                 455                 460

Gly Val Val Asn Val Gly Leu Asn Thr Thr Trp Leu Gly Ser His Leu
465                 470                 475                 480

Ala Met Ser Asn Leu Tyr Ala Tyr Gly Arg Leu Ala Trp Asp Pro Ser
                485                 490                 495

Ala Asp Ser Val Glu Leu Leu Gln Glu Trp Ile Lys Met Thr Phe Ser
            500                 505                 510

His Asp Gln Glu Val Val Asp Val Ile Thr Lys Met Ser Met Glu Ser
    515                 520                 525

Trp Pro Ala Tyr Glu Asn Tyr Ser Gly Asn Leu Gly Ile Gln Thr Leu
530                 535                 540

Thr Asp Ile Leu Leu Gly His Tyr Gly Pro Asn Pro Ala Ser Gln Asp
545                 550                 555                 560

Gly Asn Pro Trp Gly Gln Trp Thr Arg Ala Asp Ala Asp Ser Ile Gly
                565                 570                 575

Met Asp Arg Thr Val Trp Asn Gly Thr Gly Asn Ala Gly Gln Tyr Pro
            580                 585                 590

Glu Glu Val Tyr Gln Met Tyr Glu Asn Ile Asp Thr Thr Pro Asp Asn
    595                 600                 605

Leu Leu Leu Trp Phe His His Val Pro Tyr Thr Gln Arg Leu Lys Ser
    610                 615                 620
```

```
Gly Lys Thr Val Ile Gln His Phe Tyr Asp Ala His Tyr Arg Gly Ser
625                 630                 635                 640

Ala Thr Ala Gln Thr Phe Val Ser Leu Trp Lys Thr Ile Lys Gly Lys
            645                 650                 655

Ile Asp Lys Glu Arg Tyr Glu His Val Leu Phe Arg Leu Val Tyr Gln
            660                 665                 670

Ala Gly His Ala Leu Val Trp Arg Asp Ser Ile Thr Asn Phe Tyr Tyr
        675                 680                 685

Asn Lys Ser Gly Ile Pro Asp Glu Ala Gly Arg Val Gly Asn His Pro
690                 695                 700

Tyr Arg Ile Glu Ala Glu Asp Met Glu Leu Asp Gly Tyr Glu Pro Tyr
705                 710                 715                 720

Leu Val Ser Pro Phe Glu Ala Ala Ser Gly Ser His Cys Ile Val Thr
                725                 730                 735

Ser Asn Asn Ser Thr Glu Gly Arg Ala Ser Thr Pro Leu Lys Val Lys
                740                 745                 750

Asn Gly Lys Tyr Asp Ile Ala Val Asn Tyr Phe Asp Gln Ala Ile Gly
            755                 760                 765

Asn Ser Thr Trp Arg Leu Phe Leu Asp Asp Leu Val Gly Glu Trp
770                 775                 780

Lys Gly Asp Leu Glu Tyr Ile Leu Gly Arg Ala Pro Ser Pro Tyr Ile
785                 790                 795                 800

Asp Gly Gln Thr Ala Ala Arg Ile Thr Phe Lys His Val His Ile Lys
                805                 810                 815

Ser Arg Ser Thr Leu Ser Ile Val Gly Ile Pro Asp Gly Met Glu Pro
            820                 825                 830

Ala Pro Ile Asp Tyr Val Ser Ile Leu Pro Glu Gly Val Ile Asp
        835                 840                 845

<210> SEQ ID NO 3
<211> LENGTH: 2526
<212> TYPE: DNA
<213> ORGANISM: Aspergillus niger

<400> SEQUENCE: 3
atgagaggtt tgaatctctt tcaattaata ctggctcttc tgctgtccat ggtagcagcc      60
gaggatgggt acgatggctg gctcagatat gctcccgtgt cctgcgatct gcattgtcaa     120
caggctctac cgtctcatgt tgtgttgttg aacagcacca aaggaagccc aatcgagacc     180
gccggacgag aattgaaagc gggattccaa tcgattcttt cgacgaactt gacatctcgt     240
ccatttcaat gcaatagctc cgcatcaatt ctggtggcta ctctggatga gtaccgccaa     300
agatgccggg acattaatgt gcctgagctc gatcccgatg gcttctggtt acaatccgaa     360
ggggacacag ttcggatctt aggcaaggat gccagaggag ccttgtacgg agcatacgaa     420
tatctagcta tggtggcaca gcgaaatttt ctcgtgtcg cgtatgccac gagcccacat     480
gcgccgatcc gttgggtgaa tcaatgggac aacatggacg gaagcattga acgaggatac     540
ggtggtgcgt cgatattctt caaagatggc acggtggtgg aagacatggc tcctgttgag     600
caatatgcta gactgcttgc atccatccgg ataaatgcaa ttgtcgtcaa taatgtcaat     660
gcgaacgcaa cactactgct acccgagaat atgaaaggcc tgagtcgtat agcagatgca     720
tgtcgaccat acggcgttca aatcggcata tcgctgaact tgcttcacc cgaagccttg     780 ggtggtttaa atacttatga tccactcgat cctggtgtca ttgcatggtg cagaatatc     840 actgatagtc tctataccta tgtaccagac atggctgggt acctcgtcaa agccgactca     900
```

```
gagggccagc caggtcctga tacatacaat cgcacactct cacaaggggc aaatctgttc    960

gctcgtgccc tgcaaccgta tgggggtgtg cttatgtacc gtgctttcgt ctatgatgac   1020
aacttgaacg aatcagactg gaaggctgat cgtgctaagg cagcagtgga gtatttcaag   1080
gacctggacg gtcaattcga ggagaacgtc gtgatccaaa taaagtacgg cccgatcgac   1140
ttccaagtgc gcgagcctac ctcaccactt tttgccaacc tctaccacac caacacagcc   1200
atagagttgg aggttagtca ggagtacctg gggcagcaat gccatttggt gtacttacct   1260
ccgctctgga agacggtcct ggatttcgac ttacgcgtag accacaagcc atcgatggtc   1320
cgcgatatca tatccggtca gcgcttcaac agaacgctcg gaggctgggc agctgtcgtt   1380
aatgtgggca ccaacagaac atggctgggt agccaccttg ctatgtccaa tctgtacgct   1440
tacggtcgtt tggcgtggag tccgacagac gaatctgagc agatcctcga agactggact   1500
cgcctcacat ttggacaaaa tcaccatgtc attaacacta tctccgatat gtcaatgacc   1560
tcctggcctg cctatgaaaa ctataccggc aacctgggca tacagacact gacagacatc   1620
ttgtataccc actatggtcc aaatccagct acacaggata acaatggctg gggtcaatgg   1680
acacgtgctg atcatgattc tgtcggtatg gatcgcacaa tatggaacgg caccggctat   1740
accggtcaat acccggagga ggttgctcgc gtatacgaat cactagaaag cacgccagat   1800
gacctagtat tgtggtttca ccatgtacca tggacgcacc gtctgcactc cggagtgact   1860
gttatccagc atttctacaa cgctcactat gcgggcgcag aagctgcaca cggattcgtc   1920
agacaatggg agtctttgga agggctcatt gaccgggagc gatacgaagc catgcggtcg   1980
cgactggtct accaggcggg acactccatt gtctggcgag atgctatcaa taatttctac   2040
tacaacatga ccggaatccc agatgtggct ggacgtgtgg gtcaccatcc gtggcgcatt   2100
gaagccgaga gtatgggatt agatggatac cagacgtata cggtcagtcc gttcgaggct   2160
gcttctaata ctacagcaat tattaccact tctaattcaa cgactgggac ggcgagaact   2220
agcatcaagg ccccatcagg agtatacgac atagggggtga actactacga tctctatggc   2280
ggtcaatcga agtggacact atctgtgggt gataaggtag tgggccaatg gcttggggat   2340
atggagcata attccctagg ccatacacca tctatatact tgggtggtca ctccgccact   2400
cggattacgt ttcatggggt cggcattcgg cagggtgatc agctgaagat tgttggtgag   2460
gcgaatgggg tcgagcccgc tcccctggat tatatagtgc tactgccccc aggcttagtt   2520
gactga                                                               2526
```

<210> SEQ ID NO 4
<211> LENGTH: 841
<212> TYPE: PRT
<213> ORGANISM: Aspergillus niger

<400> SEQUENCE: 4

```
Met Arg Gly Leu Asn Leu Phe Gln Leu Ile Leu Ala Leu Leu Leu Ser
1               5                   10                  15

Met Val Ala Ala Glu Asp Gly Tyr Asp Gly Trp Leu Arg Tyr Ala Pro
            20                  25                  30

Val Ser Cys Asp Leu His Cys Gln Gln Ala Leu Pro Ser His Val Val
        35                  40                  45

Leu Leu Asn Ser Thr Lys Gly Ser Pro Ile Glu Thr Ala Gly Arg Glu
    50                  55                  60

Leu Lys Ala Gly Phe Gln Ser Ile Leu Ser Thr Asn Leu Thr Ser Arg
65                  70                  75                  80

```

```
Pro Phe Gln Cys Asn Ser Ser Ala Ser Ile Leu Val Ala Thr Leu Asp
            85                  90                  95

Glu Tyr Arg Gln Arg Cys Arg Asp Ile Asn Val Pro Glu Leu Asp Pro
            100                 105                 110

Asp Gly Phe Trp Leu Gln Ser Glu Gly Asp Thr Val Arg Ile Leu Gly
            115                 120                 125

Lys Asp Ala Arg Gly Ala Leu Tyr Gly Ala Tyr Glu Tyr Leu Ala Met
130                 135                 140

Val Ala Gln Arg Asn Phe Ser Arg Val Ala Tyr Ala Thr Ser Pro His
145                 150                 155                 160

Ala Pro Ile Arg Trp Val Asn Gln Trp Asp Asn Met Asp Gly Ser Ile
            165                 170                 175

Glu Arg Gly Tyr Gly Gly Ala Ser Ile Phe Phe Lys Asp Gly Thr Val
            180                 185                 190

Val Glu Asp Met Ala Pro Val Glu Gln Tyr Ala Arg Leu Leu Ala Ser
            195                 200                 205

Ile Arg Ile Asn Ala Ile Val Val Asn Asn Val Asn Ala Asn Ala Thr
210                 215                 220

Leu Leu Leu Pro Glu Asn Met Lys Gly Leu Ser Arg Ile Ala Asp Ala
225                 230                 235                 240

Cys Arg Pro Tyr Gly Val Gln Ile Gly Ile Ser Leu Asn Phe Ala Ser
            245                 250                 255

Pro Glu Ala Leu Gly Gly Leu Asn Thr Tyr Asp Pro Leu Asp Pro Gly
            260                 265                 270

Val Ile Ala Trp Trp Gln Asn Ile Thr Asp Ser Leu Tyr Thr Tyr Val
            275                 280                 285

Pro Asp Met Ala Gly Tyr Leu Val Lys Ala Asp Ser Glu Gly Gln Pro
            290                 295                 300

Gly Pro Asp Thr Tyr Asn Arg Thr Leu Ser Gln Gly Ala Asn Leu Phe
305                 310                 315                 320

Ala Arg Ala Leu Gln Pro Tyr Gly Gly Val Leu Met Tyr Arg Ala Phe
            325                 330                 335

Val Tyr Asp Asp Asn Leu Asn Glu Ser Asp Trp Lys Ala Asp Arg Ala
            340                 345                 350

Lys Ala Ala Val Glu Tyr Phe Lys Asp Leu Asp Gly Gln Phe Glu Glu
            355                 360                 365

Asn Val Val Ile Gln Ile Lys Tyr Gly Pro Ile Asp Phe Gln Val Arg
370                 375                 380

Glu Pro Thr Ser Pro Leu Phe Ala Asn Leu Tyr His Thr Asn Thr Ala
385                 390                 395                 400

Ile Glu Leu Glu Val Ser Gln Glu Tyr Leu Gly Gln Gln Cys His Leu
            405                 410                 415

Val Tyr Leu Pro Pro Leu Trp Lys Thr Val Leu Asp Phe Asp Leu Arg
            420                 425                 430

Val Asp His Lys Pro Ser Met Val Arg Asp Ile Ile Ser Gly Gln Arg
            435                 440                 445

Phe Asn Arg Thr Leu Gly Gly Trp Ala Ala Val Asn Val Gly Thr
450                 455                 460

Asn Arg Thr Trp Leu Gly Ser His Leu Ala Met Ser Asn Leu Tyr Ala
465                 470                 475                 480

Tyr Gly Arg Leu Ala Trp Ser Pro Thr Asp Glu Ser Glu Gln Ile Leu
            485                 490                 495
```

```
Glu Asp Trp Thr Arg Leu Thr Phe Gly Gln Asn His His Val Ile Asn
                500                 505                 510
Thr Ile Ser Asp Met Ser Met Thr Ser Trp Pro Ala Tyr Glu Asn Tyr
            515                 520                 525
Thr Gly Asn Leu Gly Ile Gln Thr Leu Thr Asp Ile Leu Tyr Thr His
        530                 535                 540
Tyr Gly Pro Asn Pro Ala Thr Gln Asp Asn Asn Gly Trp Gly Gln Trp
545                 550                 555                 560
Thr Arg Ala Asp His Asp Ser Val Gly Met Asp Arg Thr Ile Trp Asn
                565                 570                 575
Gly Thr Gly Tyr Thr Gly Gln Tyr Pro Glu Glu Val Ala Arg Val Tyr
            580                 585                 590
Glu Ser Leu Glu Ser Thr Pro Asp Asp Leu Val Leu Trp Phe His His
        595                 600                 605
Val Pro Trp Thr His Arg Leu His Ser Gly Val Thr Val Ile Gln His
610                 615                 620
Phe Tyr Asn Ala His Tyr Ala Gly Ala Glu Ala Ala His Gly Phe Val
625                 630                 635                 640
Arg Gln Trp Glu Ser Leu Glu Gly Leu Ile Asp Arg Glu Arg Tyr Glu
                645                 650                 655
Ala Met Arg Ser Arg Leu Val Tyr Gln Ala Gly His Ser Ile Val Trp
            660                 665                 670
Arg Asp Ala Ile Asn Asn Phe Tyr Tyr Asn Met Thr Gly Ile Pro Asp
        675                 680                 685
Val Ala Gly Arg Val Gly His His Pro Trp Arg Ile Glu Ala Glu Ser
690                 695                 700
Met Gly Leu Asp Gly Tyr Gln Thr Tyr Thr Val Ser Pro Phe Glu Ala
705                 710                 715                 720
Ala Ser Asn Thr Thr Ala Ile Ile Thr Thr Ser Asn Ser Thr Thr Gly
                725                 730                 735
Thr Ala Arg Thr Ser Ile Lys Ala Pro Ser Gly Val Tyr Asp Ile Gly
            740                 745                 750
Val Asn Tyr Tyr Asp Leu Tyr Gly Gly Gln Ser Lys Trp Thr Leu Ser
        755                 760                 765
Val Gly Asp Lys Val Val Gly Gln Trp Leu Gly Asp Met Glu His Asn
770                 775                 780
Ser Leu Gly His Thr Pro Ser Ile Tyr Leu Gly Gly His Ser Ala Thr
785                 790                 795                 800
Arg Ile Thr Phe His Gly Val Gly Ile Arg Gln Gly Asp Gln Leu Lys
                805                 810                 815
Ile Val Gly Glu Ala Asn Gly Val Glu Pro Ala Pro Leu Asp Tyr Ile
            820                 825                 830
Val Leu Leu Pro Pro Gly Leu Val Asp
        835                 840

<210> SEQ ID NO 5
<211> LENGTH: 2508
<212> TYPE: DNA
<213> ORGANISM: Penicillium aurantiogriseum

<400> SEQUENCE: 5
atgcgtgcac ttctcttctt cgcctccttg ggctttgcag ccgctgagaa cggcctcaat      60
ggctggctgc ggtacgcatc attaccctgt tcaggccaat gtcatcccaa cctcccttcg     120
agtatcgtca ccctcaatgc gactgagaca agtccggtat atgttgcggg gacggagttg     180
```

| | |
|---|---|
| caaagtggtc tcaaaggcgt ttatgggaag agtgtccaag tcgcacacaa caagtgcaag | 240 |
| acatcctcct cggttgttgt tggcacggtt gatcaatatc gggaaagctg tggccctgtg | 300 |
| aaaaacgtac ccgaactgga agaagatggc ttctggctcg ataccaaggg ggaaaacgtt | 360 |
| caaatccttg ggcaaaacga gagggtgct ctctatggca cctttgaata cttgtcgatg | 420 |
| ctcgcacagg gaaacttctc caaggtcgca tatgcgtcca atccttctgc cccaattcgc | 480 |
| tgggtgaatc aatgggatga cctggatgga agaatcgaac gcggctatgg tggcccctct | 540 |
| atcttcttca aggacggtca aatcgtcgac gacctaacac gggttactga atacgcccgt | 600 |
| ttgttggcct cgatcagaat caatgctgtc gtcattaaca atgtcaatgc ggatgctgct | 660 |
| ctcttgaatt ccacaaacct cgacggcgtg gctcgaatcg ctgatgtctt ccgcccatac | 720 |
| ggtatacaag tcggcctatc gctcaatttc gcatcccta aaacggatgg aggactcaac | 780 |
| acttttgatc ccctcgatgc atctgtcatc gagtggtggt cgaatattac aacccaggtc | 840 |
| tatgagcgag ttcctgacat ggctggctat ctggtcaagg ctgactcgga gggagagcca | 900 |
| ggcccccaga catataacag aacgctcgca gaagcggcga acctttcgc caagaagtc | 960 |
| cagcccacg gtggcattgt tatgtatcgc gcgtttgtct acaataagct aaacgaatca | 1020 |
| atctggacgg atgatcgtgc aaaggctgcc gtgggatttt tcaaggatct agatggcgaa | 1080 |
| tttgacgaca atgtggtgat ccaaatcaag tacgggccta ttgatttcca ggtccgtgaa | 1140 |
| ccagcatcgg cattgtttgc aaatttgttc aacaccagca tggccattga actacaggtt | 1200 |
| acgcaagaat atcttggaca acagtcgcat ttggtctatg ttgctcctct ttggaagacg | 1260 |
| atcttagact ctgacctccg cgtcgacggc cagccatcac tcgttcgcga tattgtgact | 1320 |
| ggtaaacggt tcaatcgcaa actgggtgga tcagcagctg ttgtcaacgt gggcacaaac | 1380 |
| accacctggc ttggtagcca cctgtctatg tcaaatctat atgcctacgg tcgcttagct | 1440 |
| tggaacccag cagatgatgc ccaagacatt ctgcaagact ggatcagact gacctttggg | 1500 |
| ctcgaccgga aggtacttga caccatcact cgcatgtcca tggaatcttg gcccgcctac | 1560 |
| gaacaataca gtgggaattt gggcatacag actttaacag atattttata cactcactat | 1620 |
| ggtcccaacc ctgcatccca agacaacaat ggatggggcc aatggacccg cgcagaccaa | 1680 |
| accagtattg gaatggatcg gacagtggca aacggcacag gcttttcggg ccagtatccg | 1740 |
| gatgaaatcg ctgccatgta tgagaacatc gacaccacgc cagacgatct tctactatgg | 1800 |
| ttccaccatg tgaaatacac ccatcgtctg cactcgggga agaccgttat tcaacacttc | 1860 |
| tacgatgaac actacagcgg ggcggaaact gcacagacat tccttacgca atgggaatca | 1920 |
| cttcatggca aaattgatgc tgagcgatac aatcatactc ggcacttcct agactaccag | 1980 |
| agcggtcact caattgtgtg gagagatgcg attaatgact tctattacaa tctttccggg | 2040 |
| atccctgatg aggccaagcg tgtcggccac cacccatggc gcatcgaagc ggaagatatg | 2100 |
| aagttagagg gctacaaaac ttacaccgtc agccccttcg aaacagcttc tggttcggtt | 2160 |
| gccattgtta caacttccaa cagtacagcc ggcaccgctt caaccaaaat aaactttccc | 2220 |
| tctggcacct atgaccttgc agtgaactac tacgatgtat acggtggcca gtcgcagtgg | 2280 |
| agggtctatc tgaataatca ggaaatcggc caatgggttg gcaatagtga ggataccttc | 2340 |
| agccacacac cttctgtcta tttggacgga cattcggcga ttcgtattaa gttccggggt | 2400 |
| gtcgaaatcc acaagggtga actttgaag attgtcggta tgcctgatgg cactgagccg | 2460 |
| gcgccattgg actatgtggc tttgctgccg gcgggtattg tagattag | 2508 |

```
<210> SEQ ID NO 6
<211> LENGTH: 527
<212> TYPE: PRT
<213> ORGANISM: Penicillium aurantiogriseum

<400> SEQUENCE: 6

Met Thr Arg Leu His Ala Trp Pro Leu Leu Ala Val Met Gly Ser Leu
1               5                   10                  15

Ala Leu Ala Ser Gln Asp Ala Phe Gln Ser Lys Cys Thr Asn Phe Gly
            20                  25                  30

Asn Gln Ile Asp Ile Pro Asn Val Lys Val Asn Phe Ala Glu Phe Val
        35                  40                  45

Gln Gly Gly Thr Asn Leu Ser Leu Val Asp Asn Pro Pro Ser Cys Gly
    50                  55                  60

Arg Ser Asn Gln Ala Val Ser Val Asp Leu Cys Arg Val Ala Met Ala
65                  70                  75                  80

Val Ser Thr Ser Asn Ser Ser Glu Ile Thr Leu Glu Ala Trp Phe Pro
                85                  90                  95

Arg Glu Tyr Lys Gly Arg Phe Leu Ser Thr Gly Asn Gly Gly Ile Ser
            100                 105                 110

Gly Cys Ile Gln Tyr Tyr Asp Leu Ala Tyr Thr Ala Gln Leu Gly Phe
        115                 120                 125

Ala Thr Val Gly Ala Asn Asn Gly His Asn Gly Thr Ser Gly Lys Pro
    130                 135                 140

Phe Tyr Arg Lys Pro Glu Val Ile Lys Asp Tyr Ala Tyr Arg Ser Val
145                 150                 155                 160

His Thr Gly Val Val Ile Gly Lys Glu Leu Thr Lys Gln Phe Tyr Asp
                165                 170                 175

Glu Gly Phe Lys Lys Ser Tyr Tyr Leu Gly Cys Ser Thr Gly Gly Arg
            180                 185                 190

Gln Gly Trp Lys Ser Val Gln Lys Tyr Pro Asn Asp Phe Asp Gly Val
        195                 200                 205

Val Ala Gly Ala Pro Ala Ile Asn Leu Ile Asn Leu Phe Ser Trp Ser
    210                 215                 220

Ala Arg Phe Tyr Thr Ile Thr Gly Ser Pro Thr Ser Asp Thr Phe Leu
225                 230                 235                 240

Ser Ala Asp Glu Trp Glu Ile Val His Glu Glu Ile Ile Arg Gln Cys
                245                 250                 255

Asp Thr Ile Asp Gly Ala Glu Asp Gly Ile Ile Glu Asp Pro Asp Leu
            260                 265                 270

Cys Arg Pro Val Leu Glu Thr Leu Thr Cys Asp Pro Ser Ala Ser Asp
        275                 280                 285

Lys Thr Ser Cys Leu Thr Ser Ala Gln Val Asn Thr Ala Gln Asn Val
    290                 295                 300

Leu Ser Pro Leu Tyr Gly Ile Asn Gly Ala Leu Leu Tyr Pro Arg Met
305                 310                 315                 320

Gln Pro Gly Ser Glu Val Leu Ala Ala Pro Ile Met Tyr Ser Gly Arg
                325                 330                 335

Pro Phe Ser Tyr Ser Glu Asp Trp Tyr Arg Tyr Val Tyr Asn Asn
            340                 345                 350

Pro Ser Trp Ser Gly Ala Asn Phe Thr Leu Lys Asp Ala Ala Val Ala
        355                 360                 365

Leu Ala Gln Asn Pro Tyr Asn Leu Gln Thr Trp Glu Gly Asp Ile Ser
    370                 375                 380
```

```
Pro Phe Lys Lys Thr Gly Gly Lys Ile Leu His Tyr His Gly Leu Gln
385                 390                 395                 400

Asp Gln Leu Ile Ser Ser Glu Asp Ser Lys Met Tyr Ser His Val
            405                 410                 415

Ser Asn Thr Met Lys Leu Pro Pro Asn Lys Leu Asp Glu Phe Tyr Arg
            420                 425                 430

Phe Phe Gln Ile Ser Gly Met Gly His Cys Gly Gly Asp Gly Ala
            435                 440                 445

Tyr Gly Ile Gly Gln Gly Ile Glu Thr Tyr Asp Gly Thr Asn Pro Glu
            450                 455                 460

Asp Asn Val Leu Met Ala Met Val Gln Trp Val Glu Gly Lys Ala
465                 470                 475                 480

Pro Glu Thr Val Arg Gly Ala Lys Phe Ser Asn Gly Pro Gly Ser Lys
                485                 490                 495

Val Glu Tyr Arg Arg Lys His Cys Arg Trp Pro Arg Arg Asn Val Phe
            500                 505                 510

Lys Gly Pro Gly Asn Tyr Thr Asp Glu Asn Ala Trp Gln Cys Val
            515                 520                 525

<210> SEQ ID NO 7
<211> LENGTH: 2354
<212> TYPE: DNA
<213> ORGANISM: Flavobacterium johnsoniae

<400> SEQUENCE: 7
cataatgtat ttttaaatt aaaattttat caaatagtat tattaagatg taaaatgttg      60
atacagtaaa aatgaaattt aagaataaac taattagtaa atggcttcaa taagacttgt     120
attcctgttt gtttcgattt cctttcggc tttagcgcaa aaggattata aactttggct     180
tcagtatgat aaaatcagca attcggcaat tgcttcagaa tataaaaaca atattcaggg     240 aattgttttct ttgggaaatt ctgaaacttc tcagatttcc gtaaagaat tagaaacagg     300 aatcgctgga atgctgggaa ataaaccca aattaaatca gaattaaag gagaaaacaa      360 tctgattatt ggttctcaaa aagctttaaa tcccgatttg caaaaagctc tgcagacaga     420
ttttgaaaaa ataaacaacg aaggatttat tattaaatcc atctctttta aaaataaaaa     480
acagcttatc atttcaggaa aaatgatgt tgcggttttg tacggagtct ttgatttttt     540
aaggttgctg cagaccaata aatcaattaa aaatttaaat attgccgatt caccaaaaac     600
aaatcttcga attttaaatc actgggataa tctcgatcga actgttgaac gcggctacgc     660
aggtttctct ttatggaact ggcagaaatt acctgatttt atcgatcaaa gatatattga     720
ttatgccaga gcgaatgctt caattggaat taatggaacg ttttaaccca atgtaaatgc     780
aaacgcttta atcctgactc cgcaatattt agaaaaagtt gaagctttag ctaatgtttt     840
cagatcttac ggaataaaag tttatttaac ggcaagattt tcggcaccaa tcgaaatagg     900
aaacttaaaa actgccgatc aaaagatcc ggaagtaatt aattggtgga aaataaaatc     960
ggctgaaatt tataaaagaa ttccagattt tggtgggttt ttggtgaaag ccaattcaga    1020
aggtcagccc ggcccgcaaa actacggaag agatcatgtt gacggagcta atatgctggc    1080
tgatgccgtt gcgcctttg gcggagttat tatgtggaga gcctttgtat attcagaaca    1140
tgatgcaaat gatcgtgcta acaagctta tactgaattt cagccttatg atggaaaatt    1200
caaagaaaat gtaattgttc aggttaaaaa cggagcaatc gatttcagc ctagagaacc    1260 ttttcatccg ttatttggag caatgccgaa aacgccttta atgatggagt ttcaaattac    1320
```

-continued

```
acaggaatat ctgggtttta gcacacattt ggttttctg cctaaattat ttcaggaagt      1380
tttagaatct gataccttc aaaaaggaaa aggggcaacc gttgctaaag ttattgacgg      1440
tactttatat caaaacaaat taaccggaat tgcaggcgtt gccaatatag gaaacgactt     1500
aaactggaca ggacatcctt ttttacaggc aaattggtat ggcttcggca ggctggcctg    1560
ggatccatat ttagattcag aaaccattgc cgatgaatgg ttaagaagta ccttttctaa   1620
cgatgaaaat tttattaaac ctgtaaaaaa tatcatgatg aatcgcgtg aagccgttgt    1680 caattacatg acaccgcttg gattacatca tattatggat acaggacatc attacgggcc   1740
tgggccttgg gtttctaatt tgtcaagacc agaatgaat ccaacctatt atcataaagc     1800
agacaaaaac ggaattggtt tcgaccgatc aaaatcgggt acgaatgccg tttcacaata   1860
cgcagcagaa gccgcaaatc tttttgataa tttagaaaat tgtcccgaaa aagatctttt   1920
atggtttcat catgttgcat gggattataa actgaaaaac ggacaaacac tttggaacgg   1980
cttggcattg aaataccaag aaggtgtaaa tcaggttgca gtaatgcaga atgtttggaa   2040
tcagacagaa aagtatgttg acagcgaacg ttttaacgaa gtaaaaatgt tattagaaat   2100
tcagcataaa gaagcaaat ggtggcgtga tgcctgctta ttatattttc agcaattttc    2160
aggaaaagaa cttccggctg gagtcgaaaa accaacacaa actttagagt attttaaatc   2220
attaaaattt cctttttgcac caggaaatgg ctaaaattag aacacggatg acacggattc  2280
acgatagcga acctgcgtca tccgcgtacc aaataccaaa aatatatttt taaaattatg   2340
agcaaaaaaa cggc                                                     2354
```

<210> SEQ ID NO 8
<211> LENGTH: 732
<212> TYPE: PRT
<213> ORGANISM: Flavobacterium johnsoniae

<400> SEQUENCE: 8

```
Met Lys Lys Pro Leu Gly Lys Ile Val Ala Ser Thr Ala Leu Leu Ile
1               5                   10                  15

Ser Val Ala Phe Ser Ser Ile Ala Ser Ala Gln Lys Asp Tyr Lys
            20                  25                  30

Leu Trp Leu Gln Tyr Asp Lys Ile Ser Asn Ser Ala Ile Ala Ser Glu
        35                  40                  45

Tyr Lys Asn Asn Ile Gln Gly Ile Val Ser Leu Gly Asn Ser Glu Thr
    50                  55                  60

Ser Gln Ile Ser Val Lys Glu Leu Glu Thr Gly Ile Ala Gly Met Leu
65                  70                  75                  80

Gly Asn Lys Pro Gln Ile Lys Ser Glu Ile Lys Gly Glu Asn Leu
                85                  90                  95

Ile Ile Gly Ser Gln Lys Ala Leu Asn Pro Asp Leu Gln Lys Ala Leu
            100                 105                 110

Gln Thr Asp Phe Glu Lys Ile Asn Asn Glu Gly Phe Ile Ile Lys Ser
        115                 120                 125

Ile Ser Phe Lys Asn Lys Lys Gln Leu Ile Ile Ser Gly Lys Asn Asp
    130                 135                 140

Val Ala Val Leu Tyr Gly Val Phe Asp Phe Leu Arg Leu Leu Gln Thr
145                 150                 155                 160

Asn Lys Ser Ile Lys Asn Leu Asn Ile Ala Asp Ser Pro Lys Thr Asn
                165                 170                 175

Leu Arg Ile Leu Asn His Trp Asp Asn Leu Asp Arg Thr Val Glu Arg
```

```
            180             185             190
Gly Tyr Ala Gly Phe Ser Leu Trp Asn Trp Gln Lys Leu Pro Asp Phe
            195                 200                 205

Ile Asp Gln Arg Tyr Ile Asp Tyr Ala Arg Ala Asn Ala Ser Ile Gly
    210                 215                 220

Ile Asn Gly Thr Val Leu Thr Asn Val Asn Ala Asn Ala Leu Ile Leu
225                 230                 235                 240

Thr Pro Gln Tyr Leu Glu Lys Val Glu Ala Leu Ala Asn Val Phe Arg
                245                 250                 255

Ser Tyr Gly Ile Lys Val Tyr Leu Thr Ala Arg Phe Ser Ala Pro Ile
            260                 265                 270

Glu Ile Gly Asn Leu Lys Thr Ala Asp Pro Lys Asp Pro Glu Val Ile
        275                 280                 285

Asn Trp Trp Lys Asn Lys Ser Ala Glu Ile Tyr Lys Arg Ile Pro Asp
        290                 295                 300

Phe Gly Gly Phe Leu Val Lys Ala Asn Ser Glu Gly Gln Pro Gly Pro
305                 310                 315                 320

Gln Asn Tyr Gly Arg Asp His Val Asp Gly Ala Asn Met Leu Ala Asp
                325                 330                 335

Ala Val Ala Pro Phe Gly Val Ile Met Trp Arg Ala Phe Val Tyr
                340                 345                 350

Ser Glu His Asp Ala Asn Asp Arg Ala Lys Gln Ala Tyr Thr Glu Phe
            355                 360                 365

Gln Pro Tyr Asp Gly Lys Phe Lys Glu Asn Val Ile Val Gln Val Lys
        370                 375                 380

Asn Gly Ala Ile Asp Phe Gln Pro Arg Glu Pro Phe His Pro Leu Phe
385                 390                 395                 400

Gly Ala Met Pro Lys Thr Pro Leu Met Met Glu Phe Gln Ile Thr Gln
                405                 410                 415

Glu Tyr Leu Gly Phe Ser Thr His Leu Val Phe Leu Pro Lys Leu Phe
            420                 425                 430

Gln Glu Val Leu Glu Ser Asp Thr Phe Gln Lys Gly Lys Gly Ala Thr
        435                 440                 445

Val Ala Lys Val Ile Asp Gly Thr Leu Tyr Gln Asn Lys Leu Thr Gly
    450                 455                 460

Ile Ala Gly Val Ala Asn Ile Gly Asn Asp Leu Asn Trp Thr Gly His
465                 470                 475                 480

Pro Phe Leu Gln Ala Asn Trp Tyr Gly Phe Gly Arg Leu Ala Trp Asp
                485                 490                 495

Pro Tyr Leu Asp Ser Glu Thr Ile Ala Asp Glu Trp Leu Arg Ser Thr
            500                 505                 510

Phe Ser Asn Asp Glu Asn Phe Ile Lys Pro Val Lys Asn Ile Met Met
        515                 520                 525

Glu Ser Arg Glu Ala Val Val Asn Tyr Met Thr Pro Leu Gly Leu His
    530                 535                 540

His Ile Met Asp Thr Gly His His Tyr Gly Pro Gly Pro Trp Val Ser
545                 550                 555                 560

Asn Leu Ser Arg Pro Glu Trp Asn Pro Thr Tyr Tyr His Lys Ala Asp
                565                 570                 575

Lys Asn Gly Ile Gly Phe Asp Arg Ser Lys Ser Gly Thr Asn Ala Val
            580                 585                 590

Ser Gln Tyr Ala Ala Glu Ala Ala Asn Leu Phe Asp Asn Leu Glu Asn
        595                 600                 605
```

```
Cys Pro Glu Lys Asp Leu Leu Trp Phe His His Val Ala Trp Asp Tyr
            610                 615                 620

Lys Leu Lys Asn Gly Gln Thr Leu Trp Asn Gly Leu Ala Leu Lys Tyr
625                 630                 635                 640

Gln Glu Gly Val Asn Gln Val Ala Val Met Gln Asn Val Trp Asn Gln
                645                 650                 655

Thr Glu Lys Tyr Val Asp Ser Glu Arg Phe Asn Glu Val Lys Met Leu
            660                 665                 670

Leu Glu Ile Gln His Lys Glu Ala Lys Trp Trp Arg Asp Ala Cys Leu
            675                 680                 685

Leu Tyr Phe Gln Gln Phe Ser Gly Lys Glu Leu Pro Ala Gly Val Glu
            690                 695                 700

Lys Pro Thr Gln Thr Leu Glu Tyr Phe Lys Ser Leu Lys Phe Pro Phe
705                 710                 715                 720

Ala Pro Gly Asn Gly His Gln His Gln His Gln His
                725                 730
```

<210> SEQ ID NO 9
<211> LENGTH: 1580
<212> TYPE: DNA
<213> ORGANISM: Cerrena unicolor

<400> SEQUENCE: 9

```
cttctttgta ggctaaccgt cagatcaaca aaatgttcaa gccatctttc gtagctctcg    60
cgctcgtctc gtacgcgact gctcaggctt ctgctcctca atggggtcag tgtggtggca   120
taggatggac cggacctact gcatgtccat caggctgggc atgtcagcaa cttaacgcgt   180
actactcgca gtgtctccag ggagccgcac ctgcacctgc acgtaccaca gctgcccctc   240
ctccccctcc tgctactact gccgcgcccc ctccacccac acatccgcg ccgaccggta   300
gttctcccgt agctggagca tgcggtgcca ttgcttccac cgtccccaat tacaacaacg   360
cgaagttgcc cgatccattc acttttgcca acggtactgc acttcgcaca aaggctgact   420
ggtcatgtcg tcgtgcagag atcagtgctt tgatccagaa ctacgaagct ggaactctcc   480
ctcccaagcc gcctgtcgtc actgcttcgt tctcgaagtc tggcaacaca ggtactttgg   540
ccattactgc tggtcttagc aacagccaga ctatcaaatt ctctccgaca atttcatacc   600
ctagcggtac tcctccggcc aatggctggc actgatcat tgcgtacgag ggtggtagca   660
ttcccattcc cgccggggtc gcgacattga cctatagcaa cagcgacatg gctcaacaaa   720
acagcgcctc cagcagaggc cagggtctct tctaccagct ctacggtagc acgcacagtg   780
ctagtgccat gactgcctgg gtgtggggtg tcagccgtat catcgacgct ttggagatga   840
caccgactgc acaaatcaac acccagcgga tcggcgttac gggttgctcc cgtgacggca   900
agggtgctct tatggccggt gcctttgagg agcgtatcgc tttgaccatc cctcaagagt   960
ccggctccgg aggtgatgct tgctggaggt tgtcgaagta tgagatcgat aacggcaacc  1020
aagtgcagga cgcagtcgag atcgtcggcg aaaacgtttg gttctcgacc aatttcaaca  1080
actacgttca gaaactcccc actgtgcccg aagaccacca tctcctcgct gccatggtcg  1140
cacccgggc gatgatctca ttcgagaaca ccgattactt gtggttgagc ccatgagca  1200
gcttcgggtg catgactgcc gcacataccg tctggcaggg tctcggcatt gccgactcgc  1260
acggtttcgc ccaagtcggt ggtcacgctc actgtgcatg gccgtccagc cttactcctc  1320
aactcaatgc tttcatcaac cgattcttac tcgatcaaag tgcgactaca aacgtcttca  1380
```

-continued

```
caaccaacaa ccagtttggt aaggttcagt ggaacgctgc gaactggatc acctggacca   1440
ctcccacttt gacctgattg aggccccggg tggtgtgtgg ctagtagtgg gaactaatag   1500
ttgacattgt atttaccatt ccattccata cttgcgtact agttgaagca cgcgtattct   1560
tcatatggcg ttggtctgat                                               1580
```

```
<210> SEQ ID NO 10
<211> LENGTH: 474
<212> TYPE: PRT
<213> ORGANISM: Cerrena unicolor

<400> SEQUENCE: 10
```

```
Met Phe Lys Pro Ser Phe Val Ala Leu Ala Leu Val Ser Tyr Ala Thr
1               5                   10                  15

Ala Gln Ala Ser Ala Pro Gln Trp Gly Gln Cys Gly Gly Ile Gly Trp
            20                  25                  30

Thr Gly Pro Thr Ala Cys Pro Ser Gly Trp Ala Cys Gln Gln Leu Asn
        35                  40                  45

Ala Tyr Tyr Ser Gln Cys Leu Gln Gly Ala Ala Pro Ala Pro Ala Arg
    50                  55                  60

Thr Thr Ala Ala Pro Pro Pro Pro Ala Thr Thr Ala Ala Pro Pro
65                  70                  75                  80

Pro Pro Thr Thr Ser Ala Pro Thr Gly Ser Ser Pro Val Ala Gly Ala
                85                  90                  95

Cys Gly Ala Ile Ala Ser Thr Val Pro Asn Tyr Asn Asn Ala Lys Leu
            100                 105                 110

Pro Asp Pro Phe Thr Phe Ala Asn Gly Thr Ala Leu Arg Thr Lys Ala
        115                 120                 125

Asp Trp Ser Cys Arg Arg Ala Glu Ile Ser Ala Leu Ile Gln Asn Tyr
    130                 135                 140

Glu Ala Gly Thr Leu Pro Pro Lys Pro Pro Val Val Thr Ala Ser Phe
145                 150                 155                 160

Ser Lys Ser Gly Asn Thr Gly Thr Leu Ala Ile Thr Ala Gly Leu Ser
                165                 170                 175

Asn Ser Gln Thr Ile Lys Phe Ser Pro Thr Ile Ser Tyr Pro Ser Gly
            180                 185                 190

Thr Pro Pro Ala Asn Gly Trp Pro Leu Ile Ile Ala Tyr Glu Gly Gly
        195                 200                 205

Ser Ile Pro Ile Pro Ala Gly Val Ala Thr Leu Thr Tyr Ser Asn Ser
    210                 215                 220

Asp Met Ala Gln Gln Asn Ser Ala Ser Arg Gly Gln Gly Leu Phe
225                 230                 235                 240

Tyr Gln Leu Tyr Gly Ser Thr His Ser Ala Ser Ala Met Thr Ala Trp
                245                 250                 255

Val Trp Gly Val Ser Arg Ile Ile Asp Ala Leu Glu Met Thr Pro Thr
            260                 265                 270

Ala Gln Ile Asn Thr Gln Arg Ile Gly Val Thr Gly Cys Ser Arg Asp
        275                 280                 285

Gly Lys Gly Ala Leu Met Ala Gly Ala Phe Glu Glu Arg Ile Ala Leu
    290                 295                 300

Thr Ile Pro Gln Glu Ser Gly Ser Gly Asp Ala Cys Trp Arg Leu
305                 310                 315                 320

Ser Lys Tyr Glu Ile Asp Asn Gly Asn Gln Val Gln Asp Ala Val Glu
                325                 330                 335
```

```
Ile Val Gly Glu Asn Val Trp Phe Ser Thr Asn Phe Asn Asn Tyr Val
                340                 345                 350
Gln Lys Leu Pro Thr Val Pro Glu Asp His His Leu Leu Ala Ala Met
            355                 360                 365
Val Ala Pro Arg Ala Met Ile Ser Phe Glu Asn Thr Asp Tyr Leu Trp
370                 375                 380
Leu Ser Pro Met Ser Ser Phe Gly Cys Met Thr Ala Ala His Thr Val
385                 390                 395                 400
Trp Gln Gly Leu Gly Ile Ala Asp Ser His Gly Phe Ala Gln Val Gly
                405                 410                 415
Gly His Ala His Cys Ala Trp Pro Ser Ser Leu Thr Pro Gln Leu Asn
                420                 425                 430
Ala Phe Ile Asn Arg Phe Leu Leu Asp Gln Ser Ala Thr Thr Asn Val
            435                 440                 445
Phe Thr Thr Asn Asn Gln Phe Gly Lys Val Gln Trp Asn Ala Ala Asn
450                 455                 460
Trp Ile Thr Trp Thr Thr Pro Thr Leu Thr
465                 470

<210> SEQ ID NO 11
<211> LENGTH: 1563
<212> TYPE: DNA
<213> ORGANISM: Hypocrea jecorina

<400> SEQUENCE: 11
atagagcagc gctcatagaa actagatgct agcaccttag caaagccgaa gtcgatattt      60
cgttgttcag aagtaacaag atggcttccc gcttctttgc tcttctcctt ttagcgatcc     120
caatccaggc ccaatctcca gtctggggac aatgtggtgg aattggttgg tctggcccaa     180
caacttgtgt tggaggtgcg acttgtgtat catataaccc ttattactcg caatgtattc     240
ccagtacaca ggcttcatcg agcatagcct ctacaacgct ggtcacatca tttacgacca     300
ccactgctac gaggacttcg gcatcaacgc ctccagcgag cagtacaggt gcaggcggcg     360
caacatgctc agcactgccg ggctccatta ccctgagatc aacgcaaag ctcaacgatc      420 tgtttacaat gttcaatgga gataaggtca ccacgaaaga caaattctcg tgccgccagg     480
cagagatgtc ggagctaata caacgatatg agctcggcac cctgcccgga cgaccaagca     540
ctctcacagc ctcattctcg gcaatacgt tgaccatcaa ttgcggagag gccggaaagt      600
caatttcatt cacagtcacg atcacttatc catcttccgg aacagcacca taccctgcga     660
ttatcggcta tggaggcggc agtcttccag ctcccgccgg ggttgccatg atcaacttta     720
acaatgacaa catagcagcc caagttaata caggcagccg cggacagggc aagttctacg     780
atctctacgg gagctcgcac tccgcgggcg ccatgaccgc atgggcctgg ggagtaagcc     840
gagtcattga tgctcttgag cttgtaccag gcgcaagaat agacaccacc aagattggcg     900
tgacggggtg ttcacgaaat ggcaaaggcg caatggtcgc aggtgctttc gagaaacgaa     960
tcgttctgac acttccccag gagtcgggcg ccggtggctc tgcgtgctgg aggatttcag    1020
actacttaaa gtcccaagga gccaatatcc agaccgcgtc tgagatcatt ggcgaagacc    1080
cctggttctc gactactttc aacagctacg tcaaccaagt gccggtgttg ccgtttgacc    1140
accattcgct tgctgccttg atagccccga gaggattatt cgtcatcgac aacaatattg    1200
actggctcgg cccacaaagc tgctttggct gtatgacagc tgctcacatg gcatggcaag    1260
ctttgggtgt ctcggaccac atgggctatt cgcagattgg agctcacgca cactgcgcgt    1320
```

```
tcccatcaaa ccagcaatcg caacttactg cctttgttca gaaattcttg ctgggccagt    1380
ccacaaatac ggcgattttc caaagcgact tttcggccaa tcaaagccaa tggatcgact    1440
ggacaacccc aacgctgagt tgagtcttac ggccagggaa acgcgcatat ttggcgattg    1500
gcggttcctg tattatgact tggtaaccca agccatacca agcttagcag agggtgttga    1560
aag                                                                  1563
```

<210> SEQ ID NO 12
<211> LENGTH: 460
<212> TYPE: PRT
<213> ORGANISM: Hypocrea jecorina

<400> SEQUENCE: 12

```
Met Ala Ser Arg Phe Phe Ala Leu Leu Leu Ala Ile Pro Ile Gln
1               5                   10                  15

Ala Gln Ser Pro Val Trp Gly Gln Cys Gly Gly Ile Gly Trp Ser Gly
            20                  25                  30

Pro Thr Thr Cys Val Gly Gly Ala Thr Cys Val Ser Tyr Asn Pro Tyr
        35                  40                  45

Tyr Ser Gln Cys Ile Pro Ser Thr Gln Ala Ser Ser Ile Ala Ser
50                  55                  60

Thr Thr Leu Val Thr Ser Phe Thr Thr Thr Ala Thr Arg Thr Ser
65                  70                  75                  80

Ala Ser Thr Pro Pro Ala Ser Ser Thr Gly Ala Gly Ala Thr Cys
                85                  90                  95

Ser Ala Leu Pro Gly Ser Ile Thr Leu Arg Ser Asn Ala Lys Leu Asn
            100                 105                 110

Asp Leu Phe Thr Met Phe Asn Gly Asp Lys Val Thr Thr Lys Asp Lys
        115                 120                 125

Phe Ser Cys Arg Gln Ala Glu Met Ser Glu Leu Ile Gln Arg Tyr Glu
130                 135                 140

Leu Gly Thr Leu Pro Gly Arg Pro Ser Thr Leu Thr Ala Ser Phe Ser
145                 150                 155                 160

Gly Asn Thr Leu Thr Ile Asn Cys Gly Glu Ala Gly Lys Ser Ile Ser
                165                 170                 175

Phe Thr Val Thr Ile Thr Tyr Pro Ser Ser Gly Thr Ala Pro Tyr Pro
            180                 185                 190

Ala Ile Ile Gly Tyr Gly Gly Gly Ser Leu Pro Ala Pro Ala Gly Val
        195                 200                 205

Ala Met Ile Asn Phe Asn Asn Asp Asn Ile Ala Ala Gln Val Asn Thr
    210                 215                 220

Gly Ser Arg Gly Gln Gly Lys Phe Tyr Asp Leu Tyr Gly Ser Ser His
225                 230                 235                 240

Ser Ala Gly Ala Met Thr Ala Trp Ala Trp Gly Val Ser Arg Val Ile
                245                 250                 255

Asp Ala Leu Glu Leu Val Pro Gly Ala Arg Ile Asp Thr Thr Lys Ile
            260                 265                 270

Gly Val Thr Gly Cys Ser Arg Asn Gly Lys Gly Ala Met Val Ala Gly
        275                 280                 285

Ala Phe Glu Lys Arg Ile Val Leu Thr Leu Pro Gln Glu Ser Gly Ala
    290                 295                 300

Gly Gly Ser Ala Cys Trp Arg Ile Ser Asp Tyr Leu Lys Ser Gln Gly
305                 310                 315                 320

Ala Asn Ile Gln Thr Ala Ser Glu Ile Ile Gly Glu Asp Pro Trp Phe
```

|     |     |     |     |     | 325 |     |     |     |     | 330 |     |     |     |     | 335 |     |
| --- | --- | --- | --- | --- | --- | --- | --- | --- | --- | --- | --- | --- | --- | --- | --- | --- |
| Ser | Thr | Thr | Phe | Asn | Ser | Tyr | Val | Asn | Gln | Val | Pro | Val | Leu | Pro | Phe |     |
|     |     |     | 340 |     |     |     |     | 345 |     |     |     |     | 350 |     |     |     |

Asp His His Ser Leu Ala Ala Leu Ile Ala Pro Arg Gly Leu Phe Val
        355                 360                 365

Ile Asp Asn Asn Ile Asp Trp Leu Gly Pro Gln Ser Cys Phe Gly Cys
    370                 375                 380

Met Thr Ala Ala His Met Ala Trp Gln Ala Leu Gly Val Ser Asp His
385                 390                 395                 400

Met Gly Tyr Ser Gln Ile Gly Ala His Ala His Cys Ala Phe Pro Ser
                405                 410                 415

Asn Gln Gln Ser Gln Leu Thr Ala Phe Val Gln Lys Phe Leu Leu Gly
            420                 425                 430

Gln Ser Thr Asn Thr Ala Ile Phe Gln Ser Asp Phe Ser Ala Asn Gln
        435                 440                 445

Ser Gln Trp Ile Asp Trp Thr Thr Pro Thr Leu Ser
    450                 455                 460

<210> SEQ ID NO 13
<211> LENGTH: 1491
<212> TYPE: DNA
<213> ORGANISM: Chaetomium globosum

<400> SEQUENCE: 13

```
atgaccgaag gagctaccct catttacact tccaatccct tcgtaggcgg ttgtccgaca    60
gaaacactgc ccgggcgacg ggatgcgaac atctcggggg ttattctagc gattgacggc   120
ctcactcggg cgaatggccc ccgggcctcg gtggtgatat accccgacag gccctcgccg   180
tggttctttg ccttgagcaa acaaagccgc ctagacagat cgtcgacgga acaatgcgt    240
tcccttctac acacgctcgc cgcggcagcg atcggcagcg ccggcgccga cgcccacccc   300
ctgatccccc ggcagggcgg cggcaacaac acaatccaat gccccccac cccctcgccg    360
ttcccgacct ggcagcagct cccgctgcag tcgtctctgc ccgatccttt cctgccactg   420
caatacacca cgcccggcga tgcggcggac gtggtggcgg gccgcggcga gggccgggtg   480
aagacgcccg aggagtggta ccagtgccgg cagcccgaga tcctgcacat gctgcaggag   540
taccagtacg gctactaccc ggaccacggc caggagacgg tgcaggccac gcgcagcggc   600
aacacgctga gcatcaccgt ggcggccggc ggcaagacgg gccggttcag cgcgaccgtc   660
acgctgccgt cggggggcgtc cgcgtctaag cccgcccccg tggtcatcaa catcggtggc   720
atgcagaacc aggcttatct gagtgcgggc attgccgtcg cgcagtttga ttacacctcg   780
gtggcgcccg atagcaatgc gaagacgggg gcgttctgga gcatctacaa cgggagagac   840
atcggtgtgt tgacggcctg ggcgtgggc ttccaccgca cgctcgacgc tattaacatg   900
acggtgctcg agatcgacgc cgggcgggtg ggcgtgacgg ggtgttccag gctaggaaaa   960
gcggcgctcg cggcggggct cttcgacacc cgcatcacgc tcacgatgcc catgtcgtcg  1020
ggggtgcagg gcatgggccc gtaccggtac tacagcatga gcgggcaggg cgagaacctc  1080
gagaacagca gcaggggc cggtggtgg accagcagca agctagggc gtttatcaac     1140
cactccgaga acctgccgta cgacgcgcac accatcgcgg cggccatcgc gccgagggcg  1200
ctagtcattg accaagggac gggtgaccag tttgtcaaca gcaagggcac cgccgtcgtc  1260
atctacccgg cggcgaaagt ggtgtacgac tggctgggtg cgggtgacaa gatcgccatc  1320
agcgtgcgtg ggggcgggca ttgtgatatg agcggattca catccatcct gccgtatgtg  1380
```

```
caaaagatct tctttggtac accgacgagc aaggactata acaatttggg atcctacggg    1440
tcgcctgtga cgaccgcctt cccatggggg acggctgttc ccaaggcatg a             1491
```

<210> SEQ ID NO 14
<211> LENGTH: 496
<212> TYPE: PRT
<213> ORGANISM: Chaetomium globosum

<400> SEQUENCE: 14

```
Met Thr Glu Gly Ala Thr Leu Ile Tyr Thr Ser Asn Pro Phe Val Gly
1               5                   10                  15

Gly Cys Pro Thr Glu Thr Leu Pro Gly Arg Arg Asp Ala Asn Ile Ser
                20                  25                  30

Gly Val Ile Leu Ala Ile Asp Gly Leu Thr Arg Ala Asn Gly Pro Arg
            35                  40                  45

Ala Ser Val Val Ile Tyr Pro Asp Arg Pro Ser Pro Trp Phe Phe Ala
        50                  55                  60

Leu Ser Lys Gln Ser Arg Leu Asp Arg Ser Ser Thr Glu Thr Met Arg
65                  70                  75                  80

Ser Leu Leu His Thr Leu Ala Ala Ala Ile Gly Ser Ala Gly Ala
                85                  90                  95

Asp Ala His Pro Leu Ile Pro Arg Gln Gly Gly Asn Asn Thr Ile
            100                 105                 110

Gln Cys Pro Pro Thr Pro Ser Pro Phe Pro Thr Trp Gln Gln Leu Pro
        115                 120                 125

Leu Gln Ser Ser Leu Pro Asp Pro Phe Leu Pro Leu Gln Tyr Thr Thr
130                 135                 140

Pro Gly Asp Ala Ala Asp Val Val Ala Gly Arg Gly Glu Gly Arg Val
145                 150                 155                 160

Lys Thr Pro Glu Glu Trp Tyr Gln Cys Arg Gln Pro Glu Ile Leu His
                165                 170                 175

Met Leu Gln Glu Tyr Gln Tyr Gly Tyr Tyr Pro Asp His Gly Gln Glu
            180                 185                 190

Thr Val Gln Ala Thr Arg Ser Gly Asn Thr Leu Ser Ile Thr Val Ala
        195                 200                 205

Ala Gly Gly Lys Thr Gly Arg Phe Ser Ala Thr Val Thr Leu Pro Ser
210                 215                 220

Gly Ala Ser Ala Ser Lys Pro Ala Pro Val Val Ile Asn Ile Gly Gly
225                 230                 235                 240

Met Gln Asn Gln Ala Tyr Leu Ser Ala Gly Ile Ala Val Ala Gln Phe
                245                 250                 255

Asp Tyr Thr Ser Val Ala Pro Ser Asn Ala Lys Thr Gly Ala Phe
            260                 265                 270

Trp Ser Ile Tyr Asn Gly Arg Asp Ile Gly Val Leu Thr Ala Trp Ala
        275                 280                 285

Trp Gly Phe His Arg Thr Leu Asp Ala Ile Asn Met Thr Val Leu Glu
290                 295                 300

Ile Asp Ala Gly Arg Val Gly Val Thr Gly Cys Ser Arg Leu Gly Lys
305                 310                 315                 320

Ala Ala Leu Ala Ala Gly Leu Phe Asp Thr Arg Ile Thr Leu Thr Met
                325                 330                 335

Pro Met Ser Ser Gly Val Gln Gly Met Gly Pro Tyr Arg Tyr Tyr Ser
            340                 345                 350
```

```
Met Ser Gly Gln Gly Glu Asn Leu Glu Asn Ser Lys Gln Gly Ala Gly
        355                 360                 365

Trp Trp Thr Ser Ser Lys Leu Gly Ala Phe Ile Asn His Ser Glu Asn
    370                 375                 380

Leu Pro Tyr Asp Ala His Thr Ile Ala Ala Ile Ala Pro Arg Ala
385                 390                 395                 400

Leu Val Ile Asp Gln Gly Thr Gly Asp Gln Phe Val Asn Ser Lys Gly
                405                 410                 415

Thr Ala Val Val Ile Tyr Pro Ala Ala Lys Val Val Tyr Asp Trp Leu
                420                 425                 430

Gly Ala Gly Asp Lys Ile Ala Ile Ser Val Arg Gly Gly Gly His Cys
            435                 440                 445

Asp Met Ser Gly Phe Thr Ser Ile Leu Pro Tyr Val Gln Lys Ile Phe
        450                 455                 460

Phe Gly Thr Pro Thr Ser Lys Asp Tyr Asn Asn Leu Gly Ser Tyr Gly
465                 470                 475                 480

Ser Pro Val Thr Thr Ala Phe Pro Trp Gly Thr Ala Val Pro Lys Ala
                485                 490                 495
```

POLYPEPTIDES HAVING ALPHA-GLUCURONIDASE ACTIVITY AND POLYNUCLEOTIDES ENCODING SAME

CROSS-REFERENCE TO RELATED APPLICATIONS

This application is a 35 U.S.C. 371 national application of PCT/EP2013/058293, filed on Apr. 22, 2013, which claims priority or the benefit under 35 U.S.C. 119 of European application No. 12165163.2, filed Apr. 23, 2012, and U.S. Provisional Application Ser. No. 61/638,712, filed on Apr. 26, 2012. The contents of these applications are fully incorporated herein by reference.

REFERENCE TO A SEQUENCE LISTING

This application contains a Sequence Listing in computer readable form, which is incorporated herein by reference.

BACKGROUND OF THE INVENTION

1. Field of the Invention

The present invention relates to polypeptides having alpha-glucuronidase activity, catalytic domains, binding domains and polynucleotides encoding the polypeptides, catalytic domains or binding domains. The invention also relates to nucleic acid constructs, vectors, and host cells comprising the polynucleotides as well as methods of producing and using the polypeptides, catalytic domains and binding domains.

A further aspect of the invention relates to the combined action of polypeptides having alpha-glucuronidase activity, and polypeptides having glucuronyl esterase activity.

2. Description of the Related Art

Cellulosic or xylan-containing material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

The purpose of the pretreatment is to improve the rate of production as well as the total yield of liberated sugars in the hydrolysis step. In case of chemical pretreatment, like e.g. acid pretreatment or alkali pretreatment, the type of pretreatment will have different effects on lignocelluloses structural components and thus the enzyme composition used for the hydrolysis step may differ dependent on the pretreatment method. The aim of the present method is to improve hydrolysis of pretreated xylan containing material.

The present invention provides polypeptides having alpha-glucuronidase activity and peptides having glucuronyl esterase activity and polynucleotides encoding the polypeptides. The use of polypeptides having alpha-glucuronidase activity and combinations of polypeptides having alpha-glucuronidase and polypeptides having glucuronyl esterase activity provides methods for improved hydrolysis of in particular xylan containing material.

SUMMARY OF THE INVENTION

The present invention relates to isolated polypeptide having alpha-glucuronidase activity, selected from the group consisting of:

(a) a polypeptide having at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO:2; or at least 95%, at least 96%, at least 97%, at least 98%, at least 99%, or 100% sequence identity to the mature polypeptide of SEQ ID NO:4 or at least 95%, at least 96%, at least 97%, at least 98%, at least 99%, or 100% sequence identity to the mature polypeptide of SEQ ID NO:6 or at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO:8;

(b) a polypeptide encoded by a polynucleotide that hybridizes under high stringency conditions, or very high stringency conditions with (i) the mature polypeptide coding sequence of SEQ ID NO:1, (ii) the cDNA sequence thereof, or (iii) the full-length complement of (i) or (ii); or or under very high stringency conditions with (iv) the mature polypeptide coding sequence of SEQ ID NO:3, (v) the cDNA sequence thereof, or (vi) the full-length complement of (iv) or (v);

or under very high stringency conditions with (vii) the mature polypeptide coding sequence of SEQ ID NO:5, (viii) the cDNA sequence thereof, or (ix) the full-length complement of (vii) or (viii);

or under medium stringency conditions, medium-high stringency conditions, high stringency conditions, or very high stringency conditions with (x) the mature polypeptide coding sequence of SEQ ID NO:7, (xi) the cDNA sequence thereof, or (xii) the full-length complement of (x) or (xi);

(c) a polypeptide encoded by a polynucleotide having at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:1 or the cDNA sequence thereof or having at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:3 or the cDNA sequence thereof or having at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:5 or the cDNA sequence thereof or having at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:7 or the cDNA sequence thereof.

(d) a variant of the mature polypeptide of SEQ ID NO:2, SEQ ID NO:4, SEQ ID NO:6 or SEQ ID NO:8 comprising a substitution, deletion, and/or insertion at one or more positions; and (e) a fragment of the polypeptide of (a), (b), (c) or (d) that has alpha-glucuronidase activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to a polynucleotide encoding a signal peptide comprising or consisting of amino acids 1 to 20 of SEQ ID NO:4, a polynucleotide encoding a propeptide comprising or consisting of amino acids 21 to 696 of SEQ ID NO:4, or a polynucleotide encoding a signal peptide and a propeptide comprising or consisting of amino acids 1 to 696 of SEQ ID NO:4, each of which is operably linked to a gene encoding a protein; nucleic acid constructs, expression vectors, and recombinant host cells comprising the polynucleotides; and methods of producing a protein.

The present invention also relates to isolated polypeptides having alpha-glucuronidase activity selected from the group consisting of:

(a) a polypeptide having at least 92% sequence identity to the mature polypeptide of SEQ ID NO:6;

(b) a polypeptide encoded by a polynucleotide that hybridizes under high, or very high stringency conditions with (i) the mature polypeptide coding sequence of SEQ ID NO:6, (ii) the cDNA sequence thereof, or (iii) the full-length complement of (i) or (ii);

(c) a polypeptide encoded by a polynucleotide having at least 92% sequence identity to the mature polypeptide coding sequence of SEQ ID NO:6 or the cDNA sequence thereof;

(d) a variant of the mature polypeptide of SEQ ID NO:6 comprising a substitution, deletion, and/or insertion at one or more (e.g., several) positions; and (e) a fragment of the polypeptide of (a), (b), (c) or (d) that has alpha-glucuronidase activity.

The present invention also relates to a polynucleotide encoding a signal peptide comprising or consisting of amino acids 1 to 22 of SEQ ID NO:2 or amino acids 1 to 20 of SEQ ID NO:4 or amino acids 1 to 15 of SEQ ID NO:6 or amino acids 1 to 27 of SEQ ID NO:8.

The present invention also relates to methods of inhibiting expression or producing one or more of the peptides having at least 68% such as e.g. 70%, 75%, 80%, 85%, 90%, 95%, 99% or 100% sequence identity to any of the sequences SEQ ID: NO2, SEQ ID NO: 4, SEQ ID NO: 6, SEQ ID NO: 8.

Furthermore, present invention relates to a method for degrading or converting a cellulosic material, comprising: treating the cellulosic material with an enzyme composition in the presence of the polypeptide having alpha-glucuronidase activity having at least 68% such as e.g. 70%, 75%, 80%, 85%, 90%, 95%, 99% or 100% sequence identity to any of the sequences SEQ ID NO:2, SEQ ID NO:4, SEQ ID NO:6, SEQ ID NO:8.

Present invention also relates to compositions comprising polypeptides having alpha-glucuronidase activity, selected from the group consisting of:

(a) a polypeptide having at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO:2; or at least 95%, at least 96%, at least 97%, at least 98%, at least 99%, or 100% sequence identity to the mature polypeptide of SEQ ID NO:4 or at least 95%, at least 96%, at least 97%, at least 98%, at least 99%, or 100% sequence identity to the mature polypeptide of SEQ ID NO:6 or at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO:8;

(b) a polypeptide encoded by a polynucleotide that hybridizes under high stringency conditions, or very high stringency conditions with (i) the mature polypeptide coding sequence of SEQ ID NO:1, (ii) the cDNA sequence thereof, or (iii) the full-length complement of (i) or (ii); or or under very high stringency conditions with (iv) the mature polypeptide coding sequence of SEQ ID NO:3, (v) the cDNA sequence thereof, or (vi) the full-length complement of (iv) or (v);

or under very high stringency conditions with (vii) the mature polypeptide coding sequence of SEQ ID NO:5, (viii) the cDNA sequence thereof, or (ix) the full-length complement of (vii) or (viii);

or under medium stringency conditions, medium-high stringency conditions, high stringency conditions, or very high stringency conditions with (x) the mature polypeptide coding sequence of SEQ ID NO:7, (xi) the cDNA sequence thereof, or (xii) the full-length complement of (x) or (xi);

(c) a polypeptide encoded by a polynucleotide having at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:1 or the cDNA sequence thereof or having at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:3 or the cDNA sequence thereof or having at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:5 or the cDNA sequence thereof or having at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:7 or the cDNA sequence thereof (d) a variant of the mature polypeptide of SEQ ID NO:2, SEQ ID NO:4, SEQ ID NO:6 or SEQ ID NO:8 comprising a substitution, deletion, and/or insertion at one or more positions; and (e) a fragment of the polypeptide of (a), (b), (c) or (d) that has alpha-glucuronidase activity and/or an polypeptide having glucuronyl esterase activity selected from the group consisting of:

(f) a polypeptide having at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO:10; or at least 95%, at least 96%, at least 97%, at least 98%, at least 99%, or 100% sequence identity to the mature polypeptide of SEQ ID NO:12 or at least 95%, at least 96%, at least 97%, at least 98%, at least 99%, or 100% sequence identity to the mature polypeptide of SEQ ID NO:14 or (g) a polypeptide encoded by a polynucleotide that hybridizes under high stringency conditions, or very high stringency conditions with (i) the mature polypeptide coding sequence of SEQ ID NO:9, (ii) the cDNA sequence thereof, or (iii) the full-length complement of (i) or (ii); or or under very high stringency conditions with (iv) the mature polypeptide coding sequence of SEQ ID NO:11, (v) the cDNA sequence thereof, or (vi) the full-length complement of (iv) or (v);

or under very high stringency conditions with (vii) the mature polypeptide coding sequence of SEQ ID NO:13, (viii) the cDNA sequence thereof, or (ix) the full-length complement of (vii) or (viii);

(h) a polypeptide encoded by a polynucleotide having at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:9 or the cDNA sequence thereof or having at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:11 or the cDNA sequence thereof or having at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:13 or the cDNA sequence thereof;

(i) a variant of the mature polypeptide of SEQ ID NO:10, SEQ ID NO:12 or SEQ ID NO:14 comprising a substitution, deletion, and/or insertion at one or more positions; and (j) a fragment of the polypeptide of (f), (g), (h) or (i) that has glucuronyl esterase activity.

DEFINITIONS

Figure 1:
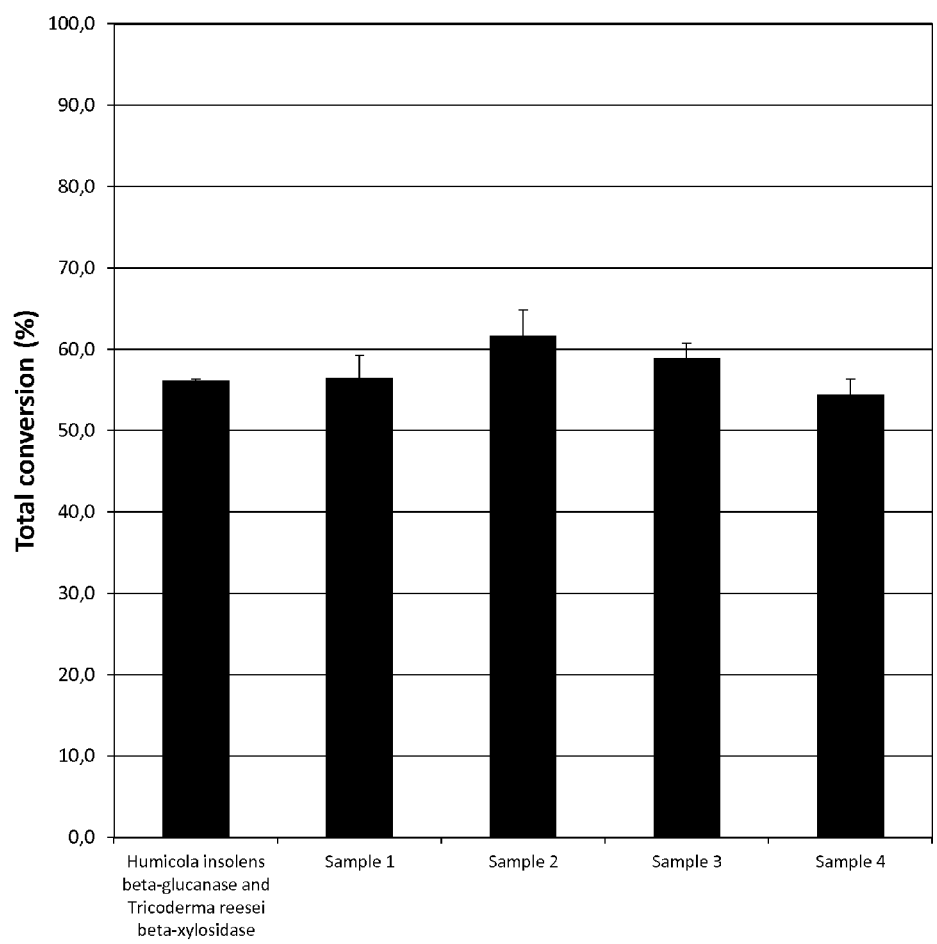
FIG. 1 shows a comparative study of the effect on percentage conversion of pretreated corn fiber after addition four alpha-glucuronidases on an enzymatic background of a beta-glucanase and β-xylosidase. Sample 1: *A. niger* (SEQ ID NO:4); Sample 2: *E. nidulans* (SEQ ID NO:2); Sample 3: *P. aurantiogriseum* (SEQ ID NO:6); Sample 4: *F. johnsoniae* (SEQ ID NO:8).

Cellulolytic activity: The term "cellulolytic activity" means a biological activity that hydrolyzes a cellulosic material. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic activity is determined by measuring the increase in hydrolysis of a cellulosic material by cellulolytic enzyme(s) under the following conditions: 1-20 mg of cellulolytic protein/g of cellulose in PCS for 3-7 days at 50-65° C. compared to a control hydrolysis without addition of cellulolytic protein. Typical conditions are 1 ml reactions, washed or unwashed PCS, 5% insoluble solids, 50 mM sodium acetate pH 5, 1 mM $MnSO_4$, 50-65° C., 72 hours, sugar analysis by AMINEX® HPX-87H column (Bio-Rad Laboratories, Inc., Hercules, Calif., USA).

Endoglucanase: The term "endoglucanase" means an endo-1,4-(1,3;1,4)-beta-D-glucan 4-glucanohydrolase (E.C. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Cellobiohydrolase: The term "cellobiohydrolase" means a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, Trichoderma reesei cellobiohydrolases: why so efficient on crystalline cellulose?, *Biochem. Soc. Trans.* 26: 173-178). For purposes of the present invention, cellobiohydrolase activity is determined using a fluorescent disaccharide derivative 4-methylumbelliferyl-β-D-lactoside according to the procedures described by van Tilbeurgh et al., 1982, *FEBS Letters* 149: 152-156 and van Tilbeurgh and Claeyssens, 1985, *FEBS Letters* 187: 283-288, at pH 5, 40° C.

Beta-glucosidase: The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenol produced per minute at 40° C., pH 5 from 1 mM p-nitrophenyl-beta-D-glucopyranoside as substrate in 100 mM sodium citrate containing 0.01% TWEEN® 20.

Cellulolytic enhancing activity: The term "cellulolytic enhancing activity" means a biological activity catalyzed by a GH61 polypeptide that enhances the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic protein and 0.5-50% w/w protein of a GH61 polypeptide having cellulolytic enhancing activity for 1-7 day at 50-65° C. compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes A/S, Bagsværd, Denmark) in the presence of 3% of total protein weight *Aspergillus oryzae* beta-glucosidase (recombinantly produced in *Aspergillus oryzae* according to WO 02/095014) or 3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Xylan degrading activity: The terms "xylan degrading activity" or "xylanolytic activity" mean a biological activity that hydrolyzes xylan-containing material. The two basic approaches for measuring xylanolytic activity include: (1) measuring the total xylanolytic activity, and (2) measuring the individual xylanolytic activities (endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase-Novel carbohydrate esterase produced by *Schizophyllum* commune, *FEBS Letters* 580 (19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined using birchwood xylan as substrate. One unit of xylanase is defined as 1.0 μmole of reducing sugar (measured in glucose equivalents as described by Lever, 1972, A new reaction for colorimetric determination of carbohydrates, Anal. Biochem 47: 273-279) produced per minute during the initial period of hydrolysis at 50° C., pH 5 from 2 g of birchwood xylan per liter as substrate in 50 mM sodium acetate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides, to remove successive D-xylose residues from the non-reducing termini. For purposes of the present invention, one unit of beta-xylosidase is defined as 1.0 μmole of p-nitrophenol produced per minute at 40° C., pH 5 from 1 mM p-nitrophenyl-beta-D-xyloside as substrate in 100 mM sodium citrate containing 0.01% TWEEN® 20.

Acetylxylan esterase: The term "acetylxylan esterase" means a carboxylesterase (EC 3.1.1.72) that catalyses the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20. One unit of acetylxylan esterase is defined as the amount of enzyme capable of releasing 1 μmole of p-nitrophenolate anion per minute at pH 5, 25° C.

Feruloyl esterase: The term "feruloyl esterase" means a 4-hydroxy-3-methoxycinnamoyl-sugar hydrolase (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

The alpha-glucuronidases of the present invention have at least 60%, e.g. at least 70%, at least 80%, at least 90%, at least 92%, at least 93%, at least 94%, at least 95%, at least 96%, at least 97%, at least 98%, at least 99% or at least 100% of the alpha-glucuronidase activity of the mature polypeptide of SEQ ID NO:2, SEQ ID NO:4, SEQ ID NO:6 or SEQ ID NO:8.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Cellulosic material: The cellulosic material can be any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is lignocellulose.

In one aspect, the cellulosic material is herbaceous material. In another aspect, the cellulosic material is agricultural residue. In another aspect, the cellulosic material is forestry residue. In another aspect, the cellulosic material is municipal solid waste. In another aspect, the cellulosic material is waste paper. In another aspect, the cellulosic material is pulp and paper mill residue.

In another aspect, the cellulosic material is corn stover. In another aspect, the cellulosic material is corn fiber. In another aspect, the cellulosic material is corn cob. In another aspect, the cellulosic material is orange peel. In another aspect, the cellulosic material is rice straw. In another aspect, the cellulosic material is wheat straw. In another aspect, the cellulosic material is switch grass. In another aspect, the cellulosic material is miscanthus. In another aspect, the cellulosic material is bagasse.

In another aspect, the cellulosic material is microcrystalline cellulose. In another aspect, the cellulosic material is bacterial cellulose. In another aspect, the cellulosic material is algal cellulose. In another aspect, the cellulosic material is cotton linter. In another aspect, the cellulosic material is amorphous phosphoric-acid treated cellulose. In another aspect, the cellulosic material is filter paper.

The cellulosic material may be used as is or may be subjected to pretreatment, using conventional methods known in the art, as described herein. In a preferred aspect, the cellulosic material is pretreated.

Pretreated corn stover: The term "PCS" or "Pretreated Corn Stover" means a cellulosic material derived from corn stover by treatment with heat and dilute sulfuric acid.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the methods of the present invention, any material containing xylan may be used. In a preferred aspect, the xylan-containing material is lignocellulose.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Binding domain: The term "binding domain" e.g., "cellulose binding domain" means the region of an enzyme that mediates binding of the enzyme to amorphous regions of a cellulose substrate. The cellulose binding domain (CBD) is typically found either at the N-terminal or at the C-terminal extremity of an alpha-glucuronidase.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic or cellulose binding domain having one or more (e.g., several) amino acids deleted from the amino and/or carboxyl terminus of a mature polypeptide or domain; wherein the fragment has alpha-glucuronidase or cellulose binding activity. In one aspect, a fragment contains at least 85%, 90%, and 95% of the number of amino acids of the mature polypeptide of SEQ ID NO:2, SEQ ID NO:4, SEQ ID NO:6 or SEQ ID NO:8.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated or purified: The term "isolated" or "purified" means a polypeptide or polynucleotide that is removed from at least one component with which it is naturally associated. For example, a polypeptide may be at least 1% pure, e.g., at least 5% pure, at least 10% pure, at least 20% pure, at least 40% pure, at least 60% pure, at least 80% pure, at least 90% pure, or at least 95% pure, as determined by SDS-PAGE, and a polynucleotide may be at least 1% pure, e.g., at least 5% pure, at least 10% pure, at least 20% pure, at least 40% pure, at least 60% pure, at least 80% pure, at least 90% pure, or at least 95% pure, as determined by agarose electrophoresis.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 702 of SEQ ID NO:2, amino acids 1 to 696 of SEQ ID NO:4, amino acids 1 to 690 of SEQ ID NO:6, amino acids 1 to 708 of SEQ ID NO:8 as predicted using SignalP (Nielsen et al., 1997, *Protein Engineering* 10:1-6) that predicts amino acids 1 to 22 of SEQ ID NO:2, 1 to 20 of SEQ ID NO:4, amino acids 21 to 690 of SEQ ID NO:4, amino acids 1 to 15 of SEQ ID NO:6, amino acids 1 to 27 of SEQ ID NO:8; are a signal peptides. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having alpha-glucuronidase activity. In one aspect, the mature polypeptide coding sequence is nucleotides 1 to 2544 of SEQ ID NO:1, nucleotides 1 to 2526 of SEQ ID NO:3, nucleotides 1 to 2508 of SEQ ID NO:5, nucleotides 1 to 2124 of SEQ ID NO:7 or the cDNA sequence thereof; based on the SignalP program (Nielsen et al., 1997, supra)] that predicts nucleotides 1 to 66 of SEQ ID NO:1, nucleotides 1 to 60 of SEQ ID NO:3, nucleotides 1 to 45 of SEQ ID NO:5, nucleotides 1 to 81 of SEQ ID NO:7, encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs the expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the —nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the —nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides deleted from the 5' and/or 3' end of a mature polypeptide coding sequence; wherein the subsequence encodes a fragment having alpha-glucuronidase activity. In one aspect, a subsequence contains at least 85%, 90%, and 95% of the number of amino acids of the mature polypeptide of SEQ ID NO:2, SEQ ID NO:4, SEQ ID NO:6 or SEQ ID NO:8.

Variant: The term "variant" means a polypeptide having alpha-glucuronidase activity comprising an alteration, i.e., a substitution, insertion, and/or deletion of one or more (e.g., several) amino acid residues at one or more positions. A substitution means a replacement of the amino acid occupying a position with a different amino acid; a deletion means removal of the amino acid occupying a position; and an insertion means adding one or more (e.g., several) amino acids, e.g., 1-5 amino acids, adjacent to the amino acid occupying a position).

Polypeptides Having Glucuronyl Esterase Activity

The term "polypeptides having glucuronyl esterase activity relates to all polypeptides having glucuronyl esterase activity. In an embodiment the term "polypeptides having glucuronyl esterase activity relates to polypeptides having glucuronyl esterase activity" polypeptides having a sequence identity to the mature polypeptide of SEQ ID NO:10 of at least 80%, e.g. at least 85%, at least 90%, at least 91%, at least 92%, at least 93%, at least 94%, at least 95%, at least 96%, at least 97%, at least 98%, at least 99%, or 100%, which have glucuronyl esterase activity. In one aspect, the polypeptides differ by no more than ten amino acids, e.g., nine amino acids, eight amino acids, seven amino acids, six amino acids, five amino acids, four amino acids, three amino acids, two amino acids, or one amino acid from the mature polypeptide of SEQ ID NO:10. A polypeptide having glucuronyl esterase activity preferably comprises or consists of the amino acid sequence of SEQ ID NO:10 or an allelic variant thereof; or is a fragment thereof having glucuronyl esterase activity. In another aspect, the polypeptide comprises or consists of the mature polypeptide of SEQ ID NO:10. In another preferred aspect, the polypeptide comprises or consists of amino acids 101 to 474 of SEQ ID NO:10.

In a further embodiment the term "polypeptides having glucuronyl esterase activity" relates to polypeptides having a sequence identity to the mature polypeptide of SEQ ID NO:12 of at least 95%, e.g., at least 96%, at least 97%, at least 98%, at least 99%, or 100%, which have glucuronyl esterase activity. In one aspect, the polypeptides differ by no more than ten amino acids, e.g., nine amino acids, eight amino acids, seven amino acids, six amino acids, five amino acids, four amino acids, three amino acids, two amino acids, or one amino acid from the mature polypeptide of SEQ ID NO:12. A polypeptide having glucuronyl esterase activity preferably comprises or consists of the amino acid sequence of SEQ ID NO:12 or an allelic variant thereof; or is a fragment thereof having glucuronyl esterase activity. In another aspect, the polypeptide comprises or consists of the mature polypeptide of SEQ ID NO:12. In another preferred aspect, the polypeptide comprises or consists of amino acids 94 to 460 of SEQ ID NO:12.

In a further embodiment the term "polypeptides having glucuronyl esterase activity" relates to polypeptides having a sequence identity to the mature polypeptide of SEQ ID NO:14 of at least 92%, e.g. at least 93%, at least 94%, at least 95%, at least 96%, at least 97%, at least 98%, at least 99%, or 100%, which have glucuronyl esterase activity. In one aspect, the polypeptides differ by no more than ten amino acids, e.g., nine amino acids, eight amino acids, seven amino acids, six amino acids, five amino acids, four amino acids, three amino acids, two amino acids, or one amino acid from the mature polypeptide of SEQ ID NO:14.

A polypeptide having glucuronyl esterase activity preferably comprises or consists of the amino acid sequence of SEQ ID NO:14 or an allelic variant thereof; or is a fragment thereof having glucuronyl esterase activity. In another aspect, the polypeptide comprises or consists of the mature polypeptide of SEQ ID NO:14. In another preferred aspect, the polypeptide comprises or consists of amino acids 21 to 392 of SEQ ID NO:14.

DETAILED DESCRIPTION OF THE INVENTION

Polypeptides Having Alpha-Glucuronidase Activity

In a further aspect, the present invention relates to the combined effect of alpha-glucuronidases and isolated polypeptides having glucuronyl esterase activity selected from the group consisting of:

(a) a polypeptide having at least 80% sequence identity to the mature polypeptide of SEQ ID NO:10;

(b) a polypeptide encoded by a polynucleotide that hybridizes under high, or very high stringency conditions with (i) the mature polypeptide coding sequence of SEQ ID NO:9, (ii) the cDNA sequence thereof, or (iii) the full-length complement of (i) or (ii);

(c) a polypeptide encoded by a polynucleotide having at least 80% sequence identity to the mature polypeptide coding sequence of SEQ ID NO:10 or the cDNA sequence thereof;

(d) a variant of the mature polypeptide of SEQ ID NO:10 comprising a substitution, deletion, and/or insertion at one or more (e.g., several) positions; and (e) a fragment of the polypeptide of (a), (b), (c) or (d) that has glucuronyl esterase activity.

Further, the present invention relates to the combined effect of alpha-glucuronidases and isolated polypeptides comprising a catalytic domain selected from the group consisting of: glucuronyl esterases (EC 2.4.1.17)

(a) a catalytic domain having at least 80% sequence identity to amino acids 101 to 474 of SEQ ID NO:10;

(b) a catalytic domain encoded by a polynucleotide that hybridizes under high, or very high stringency conditions with (i) nucleotides 33 to 1457 OF SEQ ID NO:9, (ii) the cDNA sequence thereof; or (iii) the full-length complement of (i) or (ii);

(c) a catalytic domain encoded by a polynucleotide having at least 80% sequence identity to nucleotides 33 to 1457 OF SEQ ID NO:9 or the cDNA sequence thereof;

(e) a variant of amino acids 101 to 474 of SEQ ID NO:10 comprising a substitution, deletion, and/or insertion at one or more (e.g., several) positions; and (f) a fragment of the catalytic domain of (a), (b), (c), (d) or (e) that has glucuronyl esterase activity.

Additionally, the present invention relates to the combined effect of alpha-glucuronidases and isolated polypeptides having glucuronyl esterase activity selected from the group consisting of:

(a) a polypeptide having at least 80% sequence identity to the mature polypeptide of SEQ ID NO:12;

(b) a polypeptide encoded by a polynucleotide that hybridizes under high, or very high stringency conditions with (i) the mature polypeptide coding sequence of SEQ ID NO:11, (ii) the cDNA sequence thereof, or (iii) the full-length complement of (i) or (ii);

(c) a polypeptide encoded by a polynucleotide having at least 80% sequence identity to the mature polypeptide coding sequence of SEQ ID NO:12 or the cDNA sequence thereof;

(d) a variant of the mature polypeptide of SEQ ID NO:12 comprising a substitution, deletion, and/or insertion at one or more (e.g., several) positions; and (e) a fragment of the polypeptide of (a), (b), (c) or (d) that has glucuronyl esterase activity.

The present invention also relates to isolated polypeptides comprising a catalytic domain selected from the group consisting of: glucuronyl esterases (EC 2.4.1.17)

(a) a catalytic domain having at least 80% sequence identity to amino acids 94 to 460 of SEQ ID NO:12;

(b) a catalytic domain encoded by a polynucleotide that hybridizes under high, or very high stringency conditions with (i) nucleotides 81 to 1463 of SEQ ID NO:11, (ii) the cDNA sequence thereof; or (iii) the full-length complement of (i) or (ii);

(c) a catalytic domain encoded by a polynucleotide having at least 80% sequence identity to nucleotides 81 to 1463 of SEQ ID NO:11 or the cDNA sequence thereof;

(e) a variant of amino acids 94 to 460 of SEQ ID NO:12 comprising a substitution, deletion, and/or insertion at one or more (e.g., several) positions; and (f) a fragment of the catalytic domain of (a), (b), (c), (d) or (e) that has glucuronyl esterase activity.

In a further aspect, the present invention relates to the combined effect of alpha-glucuronidases and isolated polypeptides having glucuronyl esterase activity selected from the group consisting of:

(a) a polypeptide having at least 80% sequence identity to the mature polypeptide of SEQ ID NO:14;

(b) a polypeptide encoded by a polynucleotide that hybridizes under high, or very high stringency conditions with (i) the mature polypeptide coding sequence of SEQ ID NO:14, (ii) the cDNA sequence thereof, or (iii) the full-length complement of (i) or (ii);

(c) a polypeptide encoded by a polynucleotide having at least 80% sequence identity to the mature polypeptide coding sequence of SEQ ID NO:14 or the cDNA sequence thereof;

(d) a variant of the mature polypeptide of SEQ ID NO:14 comprising a substitution, deletion, and/or insertion at one or more (e.g., several) positions; and (e) a fragment of the polypeptide of (a), (b), (c) or (d) that has glucuronyl esterase activity.

The present invention also relates to isolated polypeptides comprising a catalytic domain selected from the group consisting of: glucuronyl esterases (EC 2.4.1.17)

(a) a catalytic domain having at least 80% sequence identity to amino acids 48 to 392 of SEQ ID NO:14;

(b) a catalytic domain encoded by a polynucleotide that hybridizes under high, or very high stringency conditions with (i) nucleotides 235 to 1491 of SEQ ID NO:13, (ii) the cDNA sequence thereof; or (iii) the full-length complement of (i) or (ii);

(c) a catalytic domain encoded by a polynucleotide having at least 80% sequence identity to nucleotides 235 to 1491 of SEQ ID NO:13 or the cDNA sequence thereof;

d) a variant of the mature polypeptide of SEQ ID NO:14 comprising a substitution, deletion, and/or insertion at one or more (e.g., several) positions; and (e) a variant of amino acids 21 to 392 of SEQ ID NO:14 comprising a substitution, deletion, and/or insertion at one or more (e.g., several) positions; and (f) a fragment of the catalytic domain of (a), (b), (c), (d) or (e) that has glucuronyl esterase activity.

Furthermore, present invention relates to a method for degrading or converting a cellulosic material, comprising: treating the cellulosic material with an enzyme composition in the presence of the polypeptide having alpha-glucuronidase activity having at least 68% such as e.g. 70%, 75%, 80%, 85%, 90%, 95%, 99% or 100% sequence identity to any of the sequences SEQ ID: NO2, SEQ ID NO:4, SEQ ID NO:6, SEQ ID NO:8 and a polypeptide having glucuronyl esterase activity having at least 68% such as e.g. 70%, 75%, 80%, 85%, 90%, 95%, 99% or 100% sequence identity to any of the sequences SEQ ID NO:10, SEQ ID NO: 12 or SEQ ID NO: 14.

In an embodiment, the present invention relates to isolated polypeptides having a sequence identity to the mature polypeptide of SEQ ID NO:2 of at least 80%, e.g. at least 85%, at least 90%, at least 91%, at least 92%, at least 93%, at least 94%, at least 95%, at least 96%, at least 97%, at least 98%, at least 99%, or 100%, which have alpha-glucuronidase activity. In one aspect, the polypeptides differ by no more than ten amino acids, e.g., nine amino acids, eight amino acids, seven amino acids, six amino acids, five amino acids, four amino acids, three amino acids, two amino acids, or one amino acid from the mature polypeptide of SEQ ID NO:2.

A polypeptide of the present invention preferably comprises or consists of the amino acid sequence of SEQ ID NO:2 or an allelic variant thereof; or is a fragment thereof having alpha-glucuronidase activity. In another aspect, the polypeptide comprises or consists of the mature polypeptide of SEQ ID NO:2. In another preferred aspect, the polypeptide comprises or consists of amino acids 23 to 702 of SEQ ID NO:2.

In an embodiment, the present invention relates to isolated polypeptides having a sequence identity to the mature polypeptide of SEQ ID NO:4 of at least 95%, e.g. at least 96%, at least 97%, at least 98%, at least 99%, or 100%, which have alpha-glucuronidase activity. In one aspect, the polypeptides differ by no more than ten amino acids, e.g., nine amino acids, eight amino acids, seven amino acids, six amino acids, five amino acids, four amino acids, three amino acids, two amino acids, or one amino acid from the mature polypeptide of SEQ ID NO:4.

A polypeptide of the present invention preferably comprises or consists of the amino acid sequence of SEQ ID NO:4 or an allelic variant thereof; or is a fragment thereof having alpha-glucuronidase activity. In another aspect, the polypeptide comprises or consists of the mature polypeptide of SEQ ID NO:4. In another preferred aspect, the polypeptide comprises or consists of amino acids 21 to 696 of SEQ ID NO:4.

In an embodiment, the present invention relates to isolated polypeptides having a sequence identity to the mature polypeptide of SEQ ID NO:6 of at least 92%, e.g. at least 93%, at least 94%, at least 95%, at least 96%, at least 97%, at least 98%, at least 99%, or 100%, which have alpha-glucuronidase activity. In one aspect, the polypeptides differ by no more than ten amino acids, e.g., nine amino acids, eight amino acids, seven amino acids, six amino acids, five amino acids, four amino acids, three amino acids, two amino acids, or one amino acid from the mature polypeptide of SEQ ID NO:6.

A polypeptide of the present invention preferably comprises or consists of the amino acid sequence of SEQ ID NO:6 or an allelic variant thereof; or is a fragment thereof having alpha-glucuronidase activity. In another aspect, the polypeptide comprises or consists of the mature polypeptide of SEQ ID NO:6. In another preferred aspect, the polypeptide comprises or consists of amino acids 16 to 690 of SEQ ID NO:6.

In an embodiment, the present invention relates to isolated polypeptides having a sequence identity to the mature polypeptide of SEQ ID NO:8 of at least 68%, e.g. at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have alpha-glucuronidase activity. In one aspect, the polypeptides differ by no more than ten amino acids, e.g., nine amino acids, eight amino acids, seven amino acids, six amino acids, five amino acids, four amino acids, three amino acids, two amino acids, or one amino acid from the mature polypeptide of SEQ ID NO:8.

A polypeptide of the present invention preferably comprises or consists of the amino acid sequence of SEQ ID NO:8 or an allelic variant thereof; or is a fragment thereof having alpha-glucuronidase activity. In another aspect, the polypeptide comprises or consists of the mature polypeptide of SEQ ID NO:8. In another preferred aspect, the polypeptide comprises or consists of amino acids 33 to 708 of SEQ ID NO:8.

In another embodiment, the present invention relates to isolated polypeptides having alpha-glucuronidase activity that are encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO:1, SEQ ID NO:3, SEQ ID NO:5, SEQ ID NO:7 (ii) the cDNA sequence thereof, or (iii) the full-length complement of (i) or (ii) (Sambrook et al., 1989, *Molecular Cloning, A Laboratory Manual,* 2d edition, Cold Spring Harbor, N.Y.).

The polynucleotide of SEQ ID NO:1, SEQ ID NO:3, SEQ ID NO:5, SEQ ID NO:7 or a subsequence thereof, as well as the polypeptide of SEQ ID NO:2, SEQ ID NO:4, SEQ ID NO:6, SEQ ID NO:8 or a fragment thereof, may be used to design nucleic acid probes to identify and clone DNA encoding polypeptides having alpha-glucuronidase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having alpha-glucuronidase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO:1, SEQ ID NO:3, SEQ ID NO:5, SEQ ID NO:7 or a subsequence thereof, the carrier material is preferably used in a Southern blot.

For purposes of the present invention, hybridization indicates that the polynucleotide hybridizes to a labeled nucleic acid probe corresponding to (i) SEQ ID NO:1, SEQ ID NO:3, SEQ ID NO:5, SEQ ID NO:7; (ii) the mature polypeptide coding sequence of SEQ ID NO:1, SEQ ID NO:3, SEQ ID NO:5, SEQ ID NO:7; (iii) the cDNA sequence; (iv) the full-length complement thereof; or (v) a subsequence thereof; under very low to very high stringency conditions. Molecules to which the nucleic acid probe hybridizes under these conditions can be detected using, for example, X-ray film.

In another aspect, the nucleic acid probe is a polynucleotide that encodes the polypeptide of SEQ ID NO:2, SEQ ID NO:4, SEQ ID NO:6, SEQ ID NO:8; the mature polypeptide thereof; or a fragment thereof. In another aspect, the nucleic acid probe is SEQ ID NO:1, SEQ ID NO:3, SEQ ID NO:5, SEQ ID NO:7 or the cDNA sequence thereof.

For probes of at least 100 nucleotides in length, very low stringency conditions are defined as prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours optimally. The carrier material is finally washed three times each for 15 minutes using 2×SSC, 0.2% SDS at 45° C.

For probes of at least 100 nucleotides in length, low stringency conditions are defined as prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours optimally. The carrier material is finally washed three times each for 15 minutes using 2×SSC, 0.2% SDS at 50° C.

For probes of at least 100 nucleotides in length, medium stringency conditions are defined as prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours optimally. The carrier material is finally washed three times each for 15 minutes using 2×SSC, 0.2% SDS at 55° C.

For probes of at least 100 nucleotides in length, medium-high stringency conditions are defined as prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours optimally. The carrier material is finally washed three times each for 15 minutes using 2×SSC, 0.2% SDS at 60° C.

For probes of at least 100 nucleotides in length, high stringency conditions are defined as prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours optimally. The carrier material is finally washed three times each for 15 minutes using 2×SSC, 0.2% SDS at 65° C.

For probes of at least 100 nucleotides in length, very high stringency conditions are defined as prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours optimally. The carrier material is finally washed three times each for 15 minutes using 2×SSC, 0.2% SDS at 70° C.

In another embodiment, the present invention relates to isolated polypeptides having alpha-glucuronidase activity encoded by polynucleotides having a sequence identity to the mature polypeptide coding sequence of SEQ ID NO:1, SEQ ID NO:3, SEQ ID NO:5, SEQ ID NO:7 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO:2, SEQ ID NO:4, SEQ ID NO:6, SEQ ID NO:8 comprising a substitution, deletion, and/or insertion at one or more (e.g., several) positions. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-glucuronidase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

In an embodiment, the number of amino acid substitutions, deletions and/or insertions introduced into the mature polypeptide of SEQ ID NO:2, SEQ ID NO:4, SEQ ID NO:6, SEQ ID NO:8 is not more than 10, e.g., 1, 2, 3, 4, 5, 6, 7, 8 or 9.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

A further aspect of the invention relates to the combined action of polypeptides having alpha-glucuronidase activity, and polypeptides having glucuronyl esterase activity.

Sources of Polypeptides Having Alpha-Glucuronidase Activity

A polypeptide having alpha-glucuronidase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* polypeptide having alpha-glucuronidase activity, or a Gram-negative bacterial polypeptide such as a *Campylobacter, E. coli, Flavobacterium* e.g. *Flavobacterium johnsoniae, Fusobacterium, Helicobacter, Ilyobacter, Neisseria, Pseudomonas, Salmonella,* or *Ureaplasma* polypeptide.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide.

In another aspect, the polypeptide is a *Streptococcus equisimilis, Streptococcus pyogenes, Streptococcus uberis,* or *Streptococcus equi* subsp. *Zooepidemicus* polypeptide.

In another aspect, the polypeptide is a *Streptomyces achromogenes, Streptomyces avermitilis, Streptomyces coelicolor, Streptomyces griseus,* or *Streptomyces lividans* polypeptide.

The polypeptide may also be a fungal polypeptide. For example, the polypeptide may be a yeast polypeptide such as a *Candida, Kluyveromyces, Pichia, Saccharomyces, Schizosaccharomyces,* or *Yarrowia* polypeptide; or a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide.

In another aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide.

In another aspect, the polypeptide is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium aurantiogriseum, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* polypeptide.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Domains

The present invention also relates to catalytic domains.

In an embodiment, the catalytic domain has a sequence identity to amino acids 23 to 702 of SEQ ID NO:2 of at least 80%, e.g. at least 85%, at least 90%, at least 95%, at least 96%, at least 97%, at least 98%, at least 99%, or 100%. In an aspect, the catalytic domain comprises an amino acid sequence that differs by ten amino acids, e.g., nine amino acids, eight amino acids, seven amino acids, six amino acids, five amino acids, four amino acids, three amino acids, two amino acids, or one amino acid from amino acids 23 to 702 of SEQ ID NO:2.

The catalytic domain preferably comprises or consists of amino acids 23 to 702 of SEQ ID NO:2 or an allelic variant thereof; or is a fragment thereof having alpha-glucuronidase activity.

In another embodiment, the catalytic domain is encoded by a polynucleotide that hybridizes under very low stringency conditions, low stringency conditions, medium stringency conditions, medium-high stringency conditions, high stringency conditions, or very high stringency conditions (as defined above) with (i) the nucleotides 67 to 2544 of SEQ ID NO:1, (ii) the cDNA sequence thereof, or (iii) the full-length complement of (i) or (ii) (Sambrook et al., 1989, supra).

In another embodiment, the catalytic domain is encoded by a polynucleotide having a sequence identity to nucleotides 67 to 2544 of SEQ ID NO:1 or the cDNA sequence thereof at least 60%, e.g., at least 65%, at least 70%, at least 75%, at least 80%, at least 85%, at least 90%, at least 95%, at least 96%, at least 97%, at least 98%, at least 99%, or 100%.

In another aspect, the polynucleotide encoding the catalytic domain comprises or consists of nucleotides 67 to 2544 of SEQ ID NO:1.

In another embodiment, the catalytic domain is a variant of amino acids 23 to 702 of SEQ ID NO:2 comprising a substitution, deletion, and/or insertion at one or more (e.g., several) positions. In an embodiment, the number of amino acid substitutions, deletions and/or insertions introduced into the sequence of amino acids 23 to 702 of SEQ ID NO:2 is 10, e.g., 1, 2, 3, 4, 5, 6, 8, or 9.

In an embodiment, the catalytic domain has a sequence identity to amino acids 21 to 696 of SEQ ID NO:4 of at least 95%, e.g. at least 96%, at least 97%, at least 98%, at least 99%, or 100%. In an aspect, the catalytic domain comprises an amino acid sequence that differs by ten amino acids, e.g., nine amino acids, eight amino acids, seven amino acids, six amino acids, five amino acids, four amino acids, three amino acids, two amino acids, or one amino acid from amino acids 21 to 696 of SEQ ID NO:4.

The catalytic domain preferably comprises or consists of amino acids 21 to 696 of SEQ ID NO:4 or an allelic variant thereof; or is a fragment thereof having alpha-glucuronidase activity.

In another embodiment, the catalytic domain is encoded by a polynucleotide that hybridizes under very low stringency conditions, low stringency conditions, medium stringency conditions, medium-high stringency conditions, high stringency conditions, or very high stringency conditions (as defined above) with (i) the nucleotides 61 to 2526 of SEQ ID NO:3, (ii) the cDNA sequence thereof, or (iii) the full-length complement of (i) or (ii) (Sambrook et al., 1989, supra).

In another embodiment, the catalytic domain is encoded by a polynucleotide having a sequence identity to nucleotides 61 to 2526 of SEQ ID NO:3 or the cDNA sequence thereof at least 60%, e.g., at least 65%, at least 70%, at least 75%, at least 80%, at least 85%, at least 90%, at least 95%, at least 96%, at least 97%, at least 98%, at least 99%, or 100%.

In another aspect, the polynucleotide encoding the catalytic domain comprises or consists of nucleotides 61 to 2526 of SEQ ID NO:3.

In another embodiment, the catalytic domain is a variant of amino acids 21 to 696 of SEQ ID NO:4 comprising a substitution, deletion, and/or insertion at one or more (e.g., several) positions. In an embodiment, the number of amino acid substitutions, deletions and/or insertions introduced into the sequence of amino acids 21 to 696 of SEQ ID NO:4 is 10, e.g., 1, 2, 3, 4, 5, 6, 8, or 9.

In an embodiment, the catalytic domain has a sequence identity to amino acids 16 to 690 of SEQ ID NO:6 of at least 90%, e.g. at least 95%, at least 96%, at least 97%, at least 98%, at least 99%, or 100%. In an aspect, the catalytic domain comprises an amino acid sequence that differs by ten amino acids, e.g., nine amino acids, eight amino acids, seven amino acids, six amino acids, five amino acids, four amino acids, three amino acids, two amino acids, or one amino acid from amino acids 16 to 690 of SEQ ID NO:6.

The catalytic domain preferably comprises or consists of amino acids 16 to 690 of SEQ ID NO:6 or an allelic variant thereof; or is a fragment thereof having alpha-glucuronidase activity.

In another embodiment, the catalytic domain is encoded by a polynucleotide that hybridizes under very low stringency conditions, low stringency conditions, medium stringency conditions, medium-high stringency conditions, high stringency conditions, or very high stringency conditions (as defined above) with (i) the nucleotides 46 to 2508 of SEQ ID NO:5, (ii) the cDNA sequence thereof, or (iii) the full-length complement of (i) or (ii) (Sambrook et al., 1989, supra).

In another embodiment, the catalytic domain is encoded by a polynucleotide having a sequence identity to nucleotides 46 to 2508 of SEQ ID NO:5 or the cDNA sequence thereof at least 60%, e.g., at least 65%, at least 70%, at least 75%, at least 80%, at least 85%, at least 90%, at least 95%, at least 96%, at least 97%, at least 98%, at least 99%, or 100%.

In another aspect, the polynucleotide encoding the catalytic domain comprises or consists of nucleotides 46 to 2508 of SEQ ID NO:5.

In another embodiment, the catalytic domain is a variant of amino acids 21 to 690 of SEQ ID NO:6 comprising a substitution, deletion, and/or insertion at one or more (e.g., several) positions. In an embodiment, the number of amino acid substitutions, deletions and/or insertions introduced into the sequence of amino acids 16 to 690 of SEQ ID NO:6 is 10, e.g., 1, 2, 3, 4, 5, 6, 8, or 9.

In an embodiment, the catalytic domain has a sequence identity to amino acids 33 to 708 of SEQ ID NO:8 of at least 70%, e.g. at least 75%, at least 80%, at least 85%, at least 90%, at least 95%, at least 96%, at least 97%, at least 98%, at least 99%, or 100%. In an aspect, the catalytic domain comprises an amino acid sequence that differs by ten amino acids, e.g., nine amino acids, eight amino acids, seven amino acids, six amino acids, five amino acids, four amino acids, three amino acids, two amino acids, or one amino acid from amino acids 33 to 708 of SEQ ID NO:8.

The catalytic domain preferably comprises or consists of amino acids 33 to 708 of SEQ ID NO:8 or an allelic variant thereof; or is a fragment thereof having alpha-glucuronidase activity.

In another embodiment, the catalytic domain is encoded by a polynucleotide that hybridizes under very low stringency conditions, low stringency conditions, medium stringency conditions, medium-high stringency conditions, high stringency conditions, or very high stringency conditions (as defined above) with (i) the nucleotides 82 to 2124 of SEQ ID NO:7, (ii) the cDNA sequence thereof, or (iii) the full-length complement of (i) or (ii) (Sambrook et al., 1989, supra).

In another embodiment, the catalytic domain is encoded by a polynucleotide having a sequence identity to nucleotides 82 to 2124 of SEQ ID NO:7 or the cDNA sequence thereof at least 60%, e.g., at least 65%, at least 70%, at least 75%, at least 80%, at least 85%, at least 90%, at least 95%, at least 96%, at least 97%, at least 98%, at least 99%, or 100%.

In another aspect, the polynucleotide encoding the catalytic domain comprises or consists of nucleotides 82 to 2124 of SEQ ID NO:7.

In another embodiment, the catalytic domain is a variant of amino acids 33 to 708 of SEQ ID NO:8 comprising a substitution, deletion, and/or insertion at one or more (e.g., several) positions. In an embodiment, the number of amino acid substitutions, deletions and/or insertions introduced into the sequence of amino acids 33 to 708 of SEQ ID NO:8 is 10, e.g., 1, 2, 3, 4, 5, 6, 8, or 9.

The present invention also relates to cellulose binding domains.

In another embodiment, the cellulose binding domain is encoded by a polynucleotide that hybridizes under very low stringency conditions, low stringency conditions, medium stringency conditions, medium-high stringency conditions, high stringency conditions, or very high stringency conditions (as defined above) with (i) the nucleotides of SEQ ID NO:1, SEQ ID NO:3, SEQ ID NO:5, SEQ ID NO:7 (ii) the cDNA sequence thereof, or (iii) the full-length complement of (i) or (ii) (Sambrook et al., 1989, supra).

In another embodiment, the cellulose binding domain is a variant of SEQ ID NO:2 comprising a substitution, deletion, and/or insertion at one or more (e.g., several) positions. In an aspect, the number of amino acid substitutions, deletions and/or insertions introduced into SEQ ID NO:2, SEQ ID NO:4, SEQ ID NO:5, SEQ ID NO:8 is 10, e.g., 1, 2, 3, 4, 5, 6, 8, or 9.

A catalytic domain operably linked to the cellulose binding domain may be from a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase. The polynucleotide encoding the catalytic domain may be obtained from any prokaryotic, eukaryotic, or other source.

Polynucleotides

The present invention also relates to isolated polynucleotides encoding a polypeptide, a catalytic domain, or cellulose binding domain of the present invention, as described above.

The techniques used to isolate or clone a polynucleotide encoding a polypeptide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from any relevant microorganism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO:1, SEQ ID NO:3, SEQ ID NO:5, SEQ ID NO:7 or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *E. coli* trc promoter (Egon et al., 1988, Gene 69: 301-315), *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American,* 242: 74-94; and in Sambrook et al., 1989, supra.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV,

*Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* gene encoding a neutral alpha-amylase in which the untranslated leader has been replaced by an untranslated leader from an *Aspergillus* gene encoding a triose phosphate isomerase; non-limiting examples include modified promoters from an *Aspergillus niger* gene encoding neutral alpha-amylase in which the untranslated leader has been replaced by an untranslated leader from an *Aspergillus nidulans* or *Aspergillus oryzae* gene encoding a triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMRI permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), using competent cells (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation and electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum,*

*Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is an *Emericella* (for SEQ ID NO:2), *Aspergillus* (for SEQ ID NO:4), *Penicillum* (for SEQ ID NO:6) or *Flavobacterium* (for SEQ ID NO:8) cell. In a more preferred aspect, the cell is an *Emericella nidulans* for (SEQ ID NO:2), *Apergillus niger* (for SEQ ID NO:4), *Penicillum aurantiogriseum* (for SEQ ID NO:6) or *Flavobacterium johnsoniae* (for SEQ ID NO:8) cell.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Mol. Biol.* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods for use in accordance with the present disclosure include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising: (a) cultivating a transgenic plant or a plant cell comprising a polynucleotide encoding the polypeptide or domain under conditions conducive for production of the polypeptide or domain; and (b) recovering the polypeptide or domain.

Removal or Reduction of Alpha-Glucuronidase Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having alpha-glucuronidase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the mature polypeptide coding sequence of SEQ ID NO:1 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising: (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially alpha-glucuronidase-free product is of particular interest in the production of eukaryotic polypeptides, in particular fungal proteins such as enzymes. The alpha-glucuronidase-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from alpha-glucuronidase activity that is produced by a method of the present invention.

Methods of Processing Cellulosic Material

The present invention also relates to methods for degrading or converting a cellulosic material, comprising: treating the cellulosic material with an enzyme composition in the presence of a polypeptide having alpha-glucuronidase activity of the present invention. In a preferred aspect, the method further comprises recovering the degraded or converted cellulosic material.

The present invention also relates to methods of producing a fermentation product, comprising: (a) saccharifying a cellulosic material with an enzyme composition in the presence of a polypeptide having alpha-glucuronidase activity of the present invention; (b) fermenting the saccharified cellulosic material with one or more (several) fermenting microorganisms to produce the fermentation product; and (c) recovering the fermentation product from the fermentation.

The present invention also relates to methods of fermenting a cellulosic material, comprising: fermenting the cellulosic material with one or more (several) fermenting microorganisms, wherein the cellulosic material is saccharified with an enzyme composition in the presence of a polypeptide having alpha-glucuronidase activity of the present invention. In a preferred aspect, the fermenting of the cellulosic material produces a fermentation product. In another preferred aspect, the method further comprises recovering the fermentation product from the fermentation.

The methods of the present invention can be used to saccharify a cellulosic material to fermentable sugars and convert the fermentable sugars to many useful substances, e.g., fuel, portable ethanol, and/or fermentation products (e.g., acids, alcohols, ketones, gases, and the like). The production of a desired fermentation product from cellulosic material typically involves pretreatment, enzymatic hydrolysis (saccharification), and fermentation.

The processing of cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF); hybrid hydrolysis and co-fermentation (HHCF); and direct microbial conversion (DMC). SHF uses separate process steps to first enzymatically hydrolyze cellulosic material to fermentable sugars, e.g., glucose, cellobiose, cellotriose, and pentose sugars, and then ferment the fermentable sugars to ethanol. In SSF, the enzymatic hydrolysis of cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: fluidized bed, upflow blanket, immobilized, and extruder type reactors for hydrolysis and/or fermentation.

Pretreatment. In practicing the methods of the present invention, any pretreatment process known in the art can be used to disrupt plant cell wall components of cellulosic material (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, pre-soaking, wetting, washing, or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, cellulosic material is heated to disrupt the plant cell wall components, including lignin, hemicellulose, and cellulose to make the cellulose and other fractions, e.g., hemicellulose, accessible to enzymes. Cellulosic material is passed to or through a reaction vessel where steam is injected to increase the temperature to the required temperature and pressure and is retained therein for the desired reaction time. Steam pretreatment is preferably done at 140-230° C., more preferably 160-200° C., and most preferably 170-190° C., where the optimal temperature range depends on any addition of a chemical catalyst. Residence time for the steam pretreatment is preferably 1-15 minutes, more preferably 3-12 minutes, and most preferably 4-10 minutes, where the optimal residence time depends on temperature range and any addition of a chemical catalyst. Steam pretreatment allows for relatively high solids loadings, so that cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, Bioresource Technology 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, cellulosic material is present during pretreatment in amounts preferably between 10-80 wt %, more preferably between 20-70 wt %, and most preferably between 30-60 wt %, such as around 50 wt %. The pretreated cellulosic material can be unwashed or washed using any method known in the art, e.g., washed with water.

Mechanical Pretreatment The term "mechanical pretreatment" refers to various types of grinding or milling (e.g., dry milling, wet milling, or vibratory ball milling).

Physical Pretreatment: The term "physical pretreatment" refers to any pretreatment that promotes the separation and/or release of cellulose, hemicellulose, and/or lignin from cellulosic material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: Cellulosic material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, cellulosic material is subjected to mechanical, chemical, or physical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from cellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification. In the hydrolysis step, also known as saccharification, the cellulosic material, e.g., pretreated, is hydrolyzed to break down cellulose and alternatively also hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a polypeptide having alpha-glucuronidase activity of the present invention. The composition can further comprise one or more (several) hemicellulolytic or xylan degrading enzymes. The enzymes of the compositions can also be added sequentially.

Enzymatic hydrolysis is preferably carried out in a suitable aqueous environment under conditions that can be readily determined by one skilled in the art. In a preferred aspect, hydrolysis is performed under conditions suitable for the activity of the enzyme(s), i.e., optimal for the enzyme(s). The hydrolysis can be carried out as a fed batch or continuous process where the pretreated cellulosic material (substrate) is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to 60° C., in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

The enzyme composition preferably comprises enzymes having cellulolytic activity and/or xylan degrading activity. In one aspect, the enzyme composition comprises one or more (several) cellulolytic enzymes. In another aspect, the enzyme composition comprises one or more (several) xylan degrading enzymes. In another aspect, the enzyme composition comprises one or more (several) cellulolytic enzymes and one or more (several) xylan degrading enzymes.

The one or more (several) cellulolytic enzymes are preferably selected from the group consisting of an endoglucanase, a cellobiohydrolase, and a beta-glucosidase. The one or more (several) xylan degrading enzymes are preferably selected from the group consisting of a xylanase, an acetyxylan esterase, a feruloyl esterase, an arabinofuranosidase, a xylosidase, and a glucuronidase.

In another aspect, the enzyme composition further or even further comprises a polypeptide having cellulolytic enhancing activity (see, for example, WO 2005/074647, WO 2005/074656, and WO 2007/089290). In another aspect, the enzyme composition may further or even further comprise one or more (several) additional enzyme activities to improve the degradation of the cellulose-containing material. Preferred additional enzymes are hemicellulases (e.g., alpha-D-glucuronidases, alpha-L-arabinofuranosidases, endo-mannanases, beta-mannosidases, alpha-galactosidases, endo-alpha-L-arabinanases, beta-galactosidases), carbohydrate-esterases (e.g., acetyl-xylan esterases, acetyl-mannan esterases, ferulic acid esterases, coumaric acid esterases, glucuronoyl esterases), pectinases, proteases, ligninolytic enzymes (e.g., laccases, manganese peroxidases, lignin peroxidases, $H_2O_2$-producing enzymes, oxidoreductases), expansins, swollenins, or mixtures thereof. In the methods of the present invention, the additional enzyme(s) can be added prior to or during fermentation, e.g., during saccharification or during or after propagation of the fermenting microorganism(s).

One or more (several) components of the enzyme composition may be wild-type proteins, recombinant proteins, or a combination of wild-type proteins and recombinant proteins. For example, one or more (several) components may be native proteins of a cell, which is used as a host cell to express recombinantly one or more (several) other components of the enzyme composition. One or more (several) components of the enzyme composition may be produced as monocomponents, which are then combined to form the enzyme composition. The enzyme composition may be a combination of multicomponent and monocomponent protein preparations.

The enzymes used in the methods of the present invention may be in any form suitable for use in the processes described herein, such as, for example, a crude fermentation broth with or without cells removed, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having alpha-glucuronidase activity depend on several factors including, but not limited to, the mixture of component cellulolytic enzymes, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In a preferred aspect, an effective amount of cellulolytic enzyme(s) to cellulosic material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulosic material.

In another preferred aspect, an effective amount of polypeptide(s) having alpha-glucuronidase activity to cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably at about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulosic material.

In another preferred aspect, an effective amount of polypeptide(s) having glucuronyl esterase activity or alpha-glucuronidase activity to cellulolytic enzyme(s) is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic enzyme(s).

The enzymes can be derived or obtained from any suitable origin, including, bacterial, fungal, yeast, plant, or mammalian origin. The term "obtained" means herein that the enzyme may have been isolated from an organism that naturally produces the enzyme as a native enzyme. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having cellulolytic enzyme activity or xylan degrading activity may be a bacterial polypeptide. For example, the polypeptide may be a gram positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, or *Oceanobacillus* polypeptide having cellulolytic enzyme activity or xylan degrading activity, or a Gram negative bacterial polypeptide such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* polypeptide having cellulolytic enzyme activity or xylan degrading activity.

In a preferred aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide having cellulolytic enzyme activity or xylan degrading activity.

In another preferred aspect, the polypeptide is a *Streptococcus equisimilis*, *Streptococcus pyogenes*, *Streptococcus uberis*, or *Streptococcus* equi subsp. *Zooepidemicus* polypeptide having cellulolytic enzyme activity or xylan degrading activity.

In another preferred aspect, the polypeptide is a *Streptomyces achromogenes*, *Streptomyces avermitilis*, *Streptomyces coelicolor*, *Streptomyces griseus*, or *Streptomyces lividans* polypeptide having cellulolytic enzyme activity or xylan degrading activity.

The polypeptide having cellulolytic enzyme activity or xylan degrading activity may also be a fungal polypeptide, and more preferably a yeast polypeptide such as a *Candida*, *Kluyveromyces*, *Pichia*, *Saccharomyces*, *Schizosaccharomy-* ces, or *Yarrowia* polypeptide having cellulolytic enzyme activity or xylan degrading activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having cellulolytic enzyme activity or xylan degrading activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having cellulolytic enzyme activity or xylan degrading activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having cellulolytic enzyme activity or xylan degrading activity.

Chemically modified or protein engineered mutants of polypeptides having cellulolytic enzyme activity or xylan degrading activity may also be used.

One or more (several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

Examples of commercial cellulolytic protein preparations suitable for use in the present invention include, for example, CELLIC™ Ctec (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), ROHAMENT™ 7069 W (Rohm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, more preferably from about 0.025 to about 4.0 wt % of solids, and most preferably from about 0.005 to about 2.0 wt % of solids. The cellulase enzymes are added in amounts effective from about 0.001 to about 5.0 wt % of solids, more preferably from about 0.025 to about 4.0 wt % of solids, and most preferably from about 0.005 to about 2.0 wt % of solids.

Examples of bacterial endoglucanases that can be used in the methods of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the methods of the present invention, include, but are not limited to, a *Trichoderma reesei* endoglucanase I (Penttila et al., 1986, *Gene* 45: 253-263; GENBANK™ accession no. M15665); *Trichoderma reesei* endoglucanase II (Saloheimo, et al., 1988, *Gene* 63:11-22; GENBANK™ accession no. M19373); *Trichoderma reesei* endoglucanase III (Okada et al., 1988, *Appl. Environ. Microbiol.* 64: 555-563; GENBANK™ accession no. AB003694); and *Trichoderma reesei* endoglucanase V (Saloheimo et al., 1994, *Molecular Microbiology* 13: 219-228; GENBANK™ accession no. Z33381); *Aspergillus aculeatus* endoglucanase (Ooi et al., 1990, *Nucleic Acids Research* 18: 5884); *Aspergillus kawachii* endoglucanase (Sakamoto et al., 1995, *Current Genetics* 27: 435-439); *Erwinia carotovara* endoglucanase (Saarilahti et al., 1990, *Gene* 90: 9-14); *Fusarium oxysporum* endoglucanase (GENBANK™ accession no. L29381); *Humicola grisea* var. *thermoidea* endoglucanase (GENBANK™ accession no. AB003107); *Melanocarpus albomyces* endoglucanase (GENBANK™ accession no. MAL515703); *Neurospora crassa* endoglucanase (GENBANK™ accession no. XM_324477); *Humicola insolens* endoglucanase V; *Myceliophthora thermophila* CBS 117.65 endoglucanase; basidiomycete CBS 495.95 endoglucanase; basidiomycete CBS 494.95 endoglucanase; *Thielavia terrestris* NRRL 8126 CEL6B endoglucanase; *Thielavia terrestris* NRRL 8126 CEL6C endoglucanase); *Thielavia terrestris* NRRL 8126 CEL7C endoglucanase; *Thielavia terrestris* NRRL 8126 CEL7E endoglucanase; *Thielavia terrestris* NRRL 8126 CEL7F endoglucanase; *Cladorrhinum foecundissimum* ATCC 62373 CEL7A endoglucanase; and *Trichoderma reesei* strain No. VTT-D-80133 endoglucanase (GENBANK™ accession no. M15665).

Examples of cellobiohydrolases useful in the methods of the present invention include, but are not limited to, *Trichoderma reesei* cellobiohydrolase I; *Trichoderma reesei* cellobiohydrolase II; *Humicola insolens* cellobiohydrolase I, *Myceliophthora thermophila* cellobiohydrolase II, *Thielavia*

*terrestris* cellobiohydrolase II (CEL6A), *Chaetomium thermophilum* cellobiohydrolase I, and *Chaetomium thermophilum* cellobiohydrolase II.

Examples of beta-glucosidases useful in the methods of the present invention include, but are not limited to, *Aspergillus oryzae* beta-glucosidase; *Aspergillus fumigatus* beta-glucosidase; *Penicillium brasilianum* IBT 20888 beta-glucosidase; *Aspergillus niger* beta-glucosidase; and *Aspergillus aculeatus* beta-glucosidase.

The *Aspergillus oryzae* polypeptide having beta-glucosidase activity can be obtained according to WO 2002/095014. The *Aspergillus fumigatus* polypeptide having beta-glucosidase activity can be obtained according to WO 2005/047499. The *Penicillium brasilianum* polypeptide having beta-glucosidase activity can be obtained according to WO 2007/019442. The *Aspergillus niger* polypeptide having beta-glucosidase activity can be obtained according to Dan et al., 2000, *J. Biol. Chem.* 275: 4973-4980. The *Aspergillus aculeatus* polypeptide having beta-glucosidase activity can be obtained according to Kawaguchi et al., 1996, *Gene* 173: 287-288.

The beta-glucosidase may be a fusion protein. In one aspect, the beta-glucosidase is the *Aspergillus oryzae* beta-glucosidase variant BG fusion protein or the *Aspergillus oryzae* beta-glucosidase fusion protein obtained according to WO 2008/057637.

Other endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in EP 495,257, EP 531,315, EP 531,372, WO 89/09259, WO 94/07998, WO 95/24471, WO 96/11262, WO 96/29397, WO 96/034108, WO 97/14804, WO 98/08940, WO 98/012307, WO 98/13465, WO 98/015619, WO 98/015633, WO 98/028411, WO 99/06574, WO 99/10481, WO 99/025846, WO 99/025847, WO 99/031255, WO 2000/009707, WO 2002/050245, WO 2002/076792, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 4,435,307, U.S. Pat. No. 5,457,046, U.S. Pat. No. 5,648,263, U.S. Pat. No. 5,686,593, U.S. Pat. No. 5,691,178, U.S. Pat. No. 5,763,254, and U.S. Pat. No. 5,776,757.

In the methods of the present invention, any GH61 polypeptide having cellulolytic enhancing activity can be used.

In a first aspect, the polypeptide having cellulolytic enhancing activity comprises the following motifs:

[ILMV]-P-X(4,5)-G-X-Y-[ILMV]-X-R-X-[EQ]-X(4)-[HNQ] and [FW]-[TF]-K-[AIV], wherein X is any amino acid, X(4,5) is any amino acid at 4 or 5 contiguous positions, and X(4) is any amino acid at 4 contiguous positions.

The polypeptide comprising the above-noted motifs may further comprise:

H-X(1,2)-G-P-X(3)-[YW]-[AILMV],
[EQ]-X-Y-X(2)-C-X-[EHQN]-[FILV]-X-[ILV], or
H-X(1,2)-G-P-X(3)-[YW]-[AILMV] and [EQ]-X-Y-X(2)-C-X-[EHQN]-[FILV]-X-[ILV], wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In a preferred aspect, the polypeptide having cellulolytic enhancing activity further comprises H-X(1,2)-G-P-X(3)-[YW]-[AILMV]. In another preferred aspect, the isolated polypeptide having cellulolytic enhancing activity further comprises [EQ]X-Y-X(2)-C-X-[EHQN]-[FILV]-X-[ILV].

In another preferred aspect, the polypeptide having cellulolytic enhancing activity further comprises H-X(1,2)-G-P-X(3)-[YW]-[AILMV] and [EQ]X-Y-X(2)-C-X-[EHQN]-[FILV]-X-[ILV].

In a second aspect, the polypeptide having cellulolytic enhancing activity comprises the following motif:

[ILMV]-P-x(4,5)-G-x-Y-[ILMV]-x-R-x-[EQ]-x(3)-A-[HNQ], wherein x is any amino acid, x(4,5) is any amino acid at 4 or 5 contiguous positions, and x(3) is any amino acid at 3 contiguous positions. In the above motif, the accepted IUPAC single letter amino acid abbreviation is employed.

Examples of polypeptides having cellulolytic enhancing activity useful in the methods of the present invention include, but are not limited to, polypeptides having cellulolytic enhancing activity from *Thielavia terrestris* (WO 2005/074647); polypeptides having cellulolytic enhancing activity from *Thermoascus aurantiacus* (WO 2005/074656); polypeptides having cellulolytic enhancing activity from *Trichoderma reesei* (WO 2007/089290); and polypeptides having cellulolytic enhancing activity from *Myceliophthora thermophila* (WO 2009/085935; WO 2009/085859; WO 2009/085864; WO 2009/085868).

Examples of commercial xylan degrading enzyme preparations suitable for use in the present invention include, for example, SHEARZYME™ (Novozymes A/S), CELLIC™ Htec (Novozymes A/S), VISCOZYME® (Novozymes A/S), ULTRAFLO® (Novozymes A/S), PULPZYME® HC (Novozymes A/S), MULTIFECT® Xylanase (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the methods of the present invention include, but are not limited to, *Aspergillus aculeatus* xylanase (GeneSeqP:AAR63790; WO 94/21785), *Aspergillus fumigatus* xylanases (WO 2006/078256), and *Thielavia terrestris* NRRL 8126 xylanases (WO 2009/079210).

Examples of beta-xylosidases useful in the methods of the present invention include, but are not limited to, *Trichoderma reesei* beta-xylosidase (UniProtKB/TrEMBL accession number Q92458), *Talaromyces emersonii* (SwissProt accession number Q8×212), and *Neurospora crassa* (SwissProt accession number Q7SOW4).

Examples of acetylxylan esterases useful in the methods of the present invention include, but are not limited to, *Hypocrea jecorina* acetylxylan esterase (WO 2005/001036), *Neurospora crassa* acetylxylan esterase (UniProt accession number q7s259), *Thielavia terrestris* NRRL 8126 acetylxylan esterase (WO 2009/042846), *Chaetomium globosum* acetylxylan esterase (Uniprot accession number Q2GWX4), *Chaetomium gracile* acetylxylan esterase (GeneSeqP accession number AAB82124), *Phaeosphaeria nodorum* acetylxylan esterase (Uniprot accession number Q0UHJ1), and *Humicola insolens* DSM 1800 acetylxylan esterase (WO 2009/073709).

Examples of ferulic acid esterases useful in the methods of the present invention include, but are not limited to, *Humicola insolens* DSM 1800 feruloyl esterase (WO 2009/076122), *Neurospora crassa* feruloyl esterase (UniProt accession number Q9HGR3), and *Neosartorya fischeri* feruloyl esterase (UniProt Accession number A1D9T4).

Examples of arabinofuranosidases useful in the methods of the present invention include, but are not limited to, *Humicola insolens* DSM 1800 arabinofuranosidase (WO 2009/073383) and *Aspergillus niger* arabinofuranosidase (GeneSeqP accession number AAR94170).

Examples of alpha-glucuronidases useful in the methods of the present invention include, but are not limited to, *Aspergillus clavatus* alpha-glucuronidase (UniProt accession number alcc12), *Trichoderma reesei* alpha-glucuronidase (Uniprot accession number Q99024), *Talaromyces emersonii* alpha-glucuronidase (UniProt accession number Q8×211), *Aspergillus niger* alpha-glucuronidase (Uniprot accession number Q96WX9), *Aspergillus terreus* alpha-glucuronidase (SwissProt accession number Q0CJP9), and *Aspergillus fumigatus* alpha-glucuronidase (SwissProt accession number Q4WW45).

The enzymes and proteins used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation. The fermentable sugars obtained from the hydrolyzed cellulosic material can be fermented by one or more (several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment $C_6$ sugars include bacterial and fungal organisms, such as yeast. Preferred yeast includes strains of the *Saccharomyces* spp., preferably *Saccharomyces cerevisiae*.

Examples of fermenting organisms that can ferment $C_5$ sugars include bacterial and fungal organisms, such as yeast. Preferred $C_5$ fermenting yeast include strains of *Pichia*, preferably *Pichia stipitis*, such as *Pichia stipitis* CBS 5773; strains of *Candida*, preferably *Candida boidinii, Candida brassicae, Candida sheatae, Candida diddensii, Candida pseudotropicalis*, or *Candida utilis*.

Other fermenting organisms include strains of *Zymomonas*, such as *Zymomonas mobilis*; *Hansenula*, such as *Hansenula anomala*; *Kluyveromyces*, such as *K. fragilis*; *Schizosaccharomyces*, such as *S. pombe*; and *E. coli*, especially *E. coli* strains that have been genetically modified to improve the yield of ethanol.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis* and *Clostridium thermocellum* (Philippidis, 1996, supra).

In a preferred aspect, the bacterium is a *Zymomonas*. In a more preferred aspect, the bacterium is *Zymomonas mobilis*. In another preferred aspect, the bacterium is a *Clostridium*. In another more preferred aspect, the bacterium is *Clostridium thermocellum*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden), and FERMIOL™ (available from DSM Specialties).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces* sp.

It is well known in the art that the organisms described above can also be used to produce other substances, as described herein.

The fermenting microorganism is typically added to the degraded lignocellulose or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the yeast and/or another microorganism is applied to the degraded cellulosic material and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., portable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products: A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); a ketone (e.g., acetone); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87(4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy, Vol.* 13(1-2), pp. 83-114, 1997, Anaerobic digestion of biomass for methane production: A review.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., portable neutral spirits, or industrial ethanol.

Signal Peptide

The present invention also relates to an isolated polynucleotide encoding a signal peptide comprising or consisting of amino acids 1 to 22 of SEQ ID NO:2, amino acids 1 to 20 of SEQ ID NO:4, amino acids 1 to 15 of SEQ ID NO:4 or amino acids 1 to 22 of SEQ ID NO:8. The polynucleotides may further comprise a gene encoding a protein, which is operably linked to the signal peptide and/or propeptide. The protein is preferably foreign to the signal peptide. In one aspect, the polynucleotide encoding the signal peptide is nucleotides 1 to 66 of SEQ ID NO:1, amino acids 1 to 60 of SEQ ID NO:3, amino acids 1 to 45 of SEQ ID NO:5, amino acids 1-81 of SEQ ID NO:7.

The present invention also relates to nucleic acid constructs, expression vectors and recombinant host cells comprising such polynucleotides.

The present invention also relates to methods of producing a protein, comprising: (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone or variant thereof, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

The present invention is further described by the following examples that should not be construed as limiting the scope of the invention.

EXAMPLES

Strains

The enzymes included herein are isolated from a diverse range of microorganisms including *Emericella nidulans* (SEQ ID NO:1+2), *Aspergillus niger* (SEQ ID NO:3+4), *Penicillum aurantiogriseum* (SEQ ID NO:5+6), *Flavobacterium johnsoniae* (SEQ ID NO:7+8), *Cerrena unicolor* (SEQ ID NO: 9+10), *Hypocrea jecorina* (SEQ ID NO:11+12), *Chaetomium globosum* (SEQ ID NO:13+14).

Media and Solutions

The reaction conditions, media and solutions provided herein are included for inspiration and may be replaced by alternative methods, reaction conditions, media where the skilled person finds it applicable.

Hydrolysis Conditions

| Conditions | |
|---|---|
| Total reaction volume | 2 ml |
| Hydrolysis time | 24 or 48 h |
| Beta-glucanase composition (*H. insolens*) | 5 mg protein/g DM |
| Beta-xylosidase (*Trichoderma reesei*) | 1 mg protein/g DM |
| alpha-glucuronidase (if added) | 1 mg protein/g DM |
| Glucuronyl esterase (if added) | 1 mg protein/g DM |
| Substrate | Pretreated corn fiber (140° C., 150 min) |
| Substrate loading | 2.5% |
| Buffer | 50 mM Succinic acid pH 5.0 |
| Instruments | Thermomixer at 50° C. and 1300 rpm |

The 0.05 g pretreated corn fiber was transferred to plastic vials. Enzymes and buffer was added and the plastic vials containing a total reaction volume of 2 ml was placed on a thermomixer at 50° C. and 1300 rprm for 24 or 48 hours.

Determination of Arabinose and Xylose

Arabinose and xylose were determined by carbohydrate hydrolysis using dilute hydrochloric acid. The pretreated corn fiber was transferred to 125 ml conical flasks and diluted to contain approximately 10% dry matter. The corn fiber sample was preheated at 100° C. in an oil bath. Hydrolysis was started by adding 5 ml of 2 M hydrochloric acid for 2 hours at 100° C. After incubation the flasks were cooled on ice and neutralized with 4 M sodium hydroxide. Samples were filtered with a MINISART® 0.2 micron syringe filter (Sartorius AG, Goettingen, Germany) and analyzed for arabinose and xylose on a DIONEX BIOLC® System (Dionex Corporation, Sunnyvale, Calif., USA).

Determination of Glucose

Glucose concentration was determined with a DIONEX® BIOLC® System according to the following method. Samples (10 µl) were loaded onto a DIONEX BIOLC® System equipped with a DIONEX® CARBOPAC™ PA1 analytical column (4×250 mm) (Dionex Corporation, Sunnyvale, Calif., USA) combined with a CARBOPAC™ PA1 guard column (4×50 mm) (Dionex Corporation, Sunnyvale, Calif., USA). The monosaccharides were separated isocratically with 10 mM potassium hydroxide at a flow rate of 1 ml per minute and detected by a pulsed electrochemical detector in the pulsed amperiometric detection mode. The potential of the electrode was programmed for +0.1 volt (t=0-0.4 second) to −2.0 volt (t=0.41-0.42 second) to 0.6 volt (t=0.43 second) and finally −0.1 volt (t=0.44-0.50 second), while integrating the resulting signal from t=0.2-0.4 second.

Determination of Glucuronic Acid

Glucuronic acid concentration was determined with a DIONEX® ICS3000® System according to the following method. Samples (10 µl) were loaded onto a DIONEX ICS3000® System equipped with a DIONEX® CARBOPAC™ PA1 analytical column (4×250 mm) (Dionex Corporation, Sunnyvale, Calif., USA) combined with a CARBOPAC™ PA1 guard column (4×50 mm) (Dionex Corporation, Sunnyvale, Calif., USA). Glucuronic acid was separated isocratically with 101 mM sodium hydroxide and 160 mM sodium acetate at a flow rate of 1 ml per minute and detected by a pulsed electrochemical detector in the pulsed amperiometric detection mode. The potential of the electrode was programmed for +0.1 volt (t=0-0.4 second) to −2.0 volt (t=0.41-0.42 second) to 0.6 volt (t=0.43 second) and finally −0.1 volt (t=0.44-0.50 second), while integrating the resulting signal from t=0.2-0.4 second. Pure glucuronic acid dissolved in deionised water was used as a standard. Standards of the following concentration were used: 5, 10, 25, 50, 100, 250 and 500 pg/ml were used to determine the concentration of glucuronic acid in the hydrolysed samples.

Example 1

Effect of Alpha-Glucuronidase on Hydrolysis of Pretreated Corn Fiber

FIG. 1 shows the conversion of pretreated corn fiber after hydrolysis for 48 hours with and without addition of alpha-glucuronidase.

As apparent from FIG. 1, addition of alpha-glucuronidase to hydrolysis mixtures comprising β-glucanase and β-xylosidase enhances the total hydrolysis.

The effect of alpha-glucuronidase on hydrolysis of pretreated corn fiber was evaluated. Corn fiber is a fraction from the wet milling of corn kernels. Corn fiber is the seed coat and residual endosperm left after starch is removed and further processed. Corn fiber was pretreated by autoclaving at 140° C. for 150 minutes. The amount of theoretical arabinose, glucose and xylose in the substrate was determined to be 114, 302, and 204 g per kg dry matter using the following methods.

A mixture of arabinose, galactose, glucose, and xylose (concentration of each component: 0.0050-0.075 g per liter) was used as a standard. Standards of the following concentration were used: 5, 10, 25, 50, 100, 250 and 500 µg/ml were used to determine the concentration of glucuronic acid in the hydrolysed samples.

The hydrolysis of the pretreated corn fiber was conducted with a *Humicola insolens* beta-glucanase and a *Trichoderma reesei* beta-xylosidase. The *Trichoderma reesei* beta-xylosidase was obtained recombinantly by expression in *Aspergillus oryzae* as described in Rasmussen et al., 2006, *Biotechnology and Bioengineering* 94: 869-876 using standard cultivation methods for *Aspergillus oryzae*.

The hydrolysis of the pretreated corn fiber was performed in 2 ml EPPENDORF® tubes (Eppendorf AG, Germany) at a temperature of 50° C. and a pH of 5.0 in 50 mM succinic acid. Samples were incubated in a THERMOMIXER® Comfort (Eppendorf AG, Germany) that subjected each sample with constant heating and mixing at 1300 rpm. The substrate amount used was 2.5 w/w % DM in a total sample volume of 2 ml. The alpha-glucuronidase was added at an enzyme loading of 1 mg enzyme per g of dry matter on top of both the *Humicola insolens* beta-glucanase and the *Trichoderma reesei* beta-xylosidase. Beta-glucanase was added at a loading of 5 mg enzyme per g of dry matter and the *Trichoderma reesei* beta-xylosidase at a loading of 1 mg enzyme per g of dry matter. Hydrolysis was terminated after 48 hours by heating the samples for 10 minutes at 100° C. in a heat block (Techne Inc., Burlington N.J., USA).

Conversion was calculated by determining the amount of sugars released from the substrate as a percentage of what was added from the start using the formula below but not including initial monomeric sugars. T-tests were performed with a two tailed distribution and equal variance of sample data.

Conversion (%)=(Sugar amount in hydrolysate/Sugar amount in added substr.)×100

Comparing the conversion of pretreated corn fiber when adding the alpha-glucuronidase at an enzyme loading of 1 mg of enzyme per gram dry matter together with 1 mg enzyme per g of dry matter of *Trichoderma reesei* beta-xylosidase and 5 mg enzyme per g of dry matter of Beta-glucanase to just adding 1 mg enzyme per g of dry matter of beta-xylosidase from *Trichoderma reesei* and 5 mg enzyme per g of dry matter of The *Humicola insolens* beta-glucanase demonstrated a significant (P≤0,0412) increase in conversion from 56.0 to 61.6 (Table 1).

TABLE 1

| Samples | Conversion | Standard deviation | T-test |
|---|---|---|---|
| *Humicola insolens* beta-glucanase and *Trichoderma reesei* beta-xylosidase | 56.0 | 0.3 | 0.0412 |
| *Humicola insolens* beta-glucanase, *Trichoderma reesei* beta-xylosidase, and *Emericella nidulans* alpha-glucuronidase | 61.1 | 3.2 | |

Example 2

Figure 2:
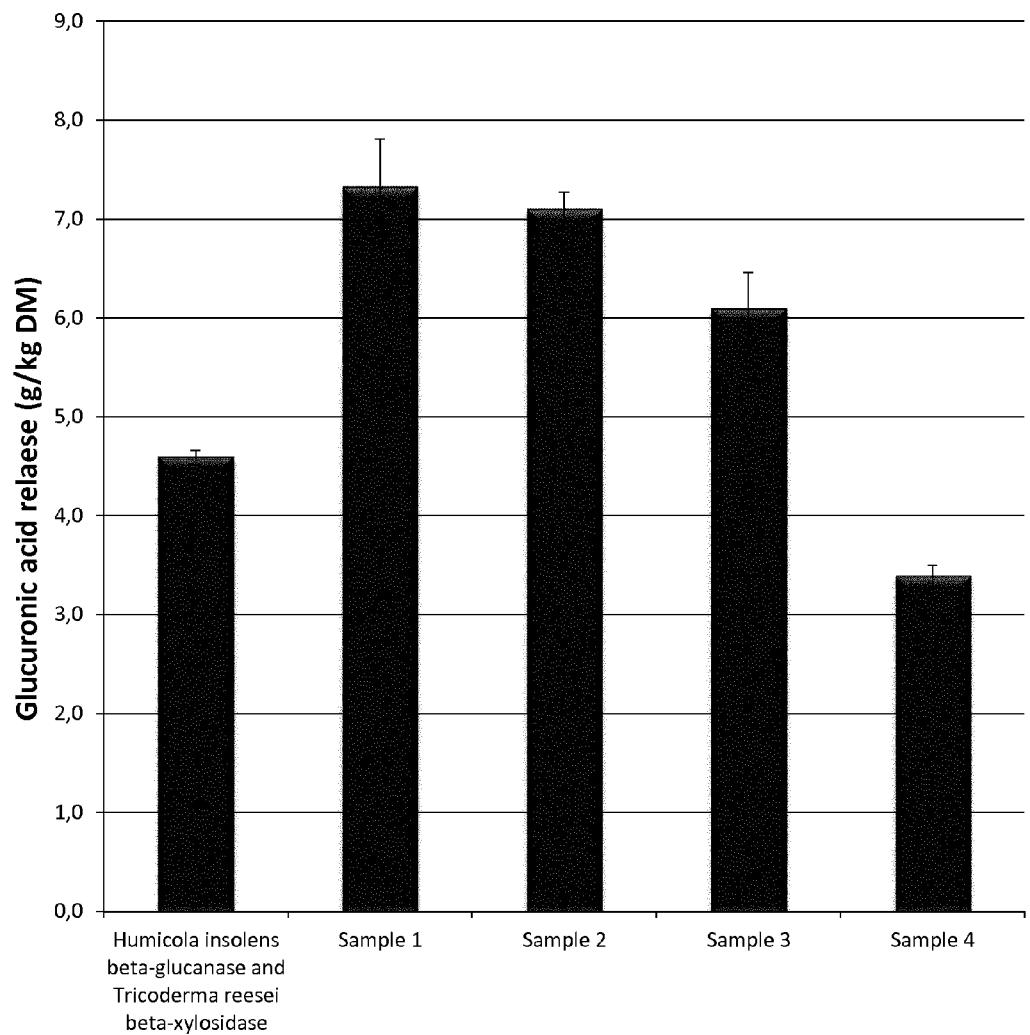
FIG. 2 shows a comparative study of the effect on the release of glucuronic acid (g/kg DM) after addition four alpha-glucuronidases on an enzymatic background of beta-glucanase and β-xylosidase. Samples: Sample 1: *A. niger* (SEQ ID NO:4); Sample 2: *E. nidulans* (SEQ ID NO:2); Sample 3: *P. aurantiogriseum* (SEQ ID NO:6); Sample 4: *F. johnsoniae* (SEQ ID NO:8).

Release of Glucuronic Acid of Pretreated Corn Fiber after Hydrolysis with Addition of Alpha-Glucuronidase As shown in FIG. 2, addition of alpha-glucuronidase stimulates the release of glucuronic acid during hydrolysis of pretreated corn fiber.

Comparing the release of glucuronic acid from pretreated corn fiber when adding the *Emericella nidulans* alpha-glucuronidase at an enzyme loading of 1 mg of enzyme per gram dry matter together with 1 mg enzyme per g of dry matter of *Trichoderma reesei* beta-xylosidase and 5 mg enzyme per g of dry matter of *Humicola insolens* beta-glucanase to just adding 1 mg enzyme per g of dry matter of beta-xylosidase from *Trichoderma reesei* and 5 mg enzyme per g of dry matter of *Humicola insolens* beta-glucanase demonstrated a significant (P≥0,00002) increase in glucuronic acid release from 4.6 to 7.1 g/kg DM (Table 2).

TABLE 2

| Samples | Mean release (g/kg DM) | Standard deviation | T-test |
|---|---|---|---|
| *Humicola insolens* beta-glucanase and *Trichoderma reesei* beta-xylosidase | 4.6 | 0.1 | 0.00002 |
| *Humicola insolens* beta-glucanase, *Trichoderma reesei* beta-xylosidase, and *Emericella nidulans* alpha-glucuronidase | 7.1 | 0.2 | |

Example 3

Figure 3:
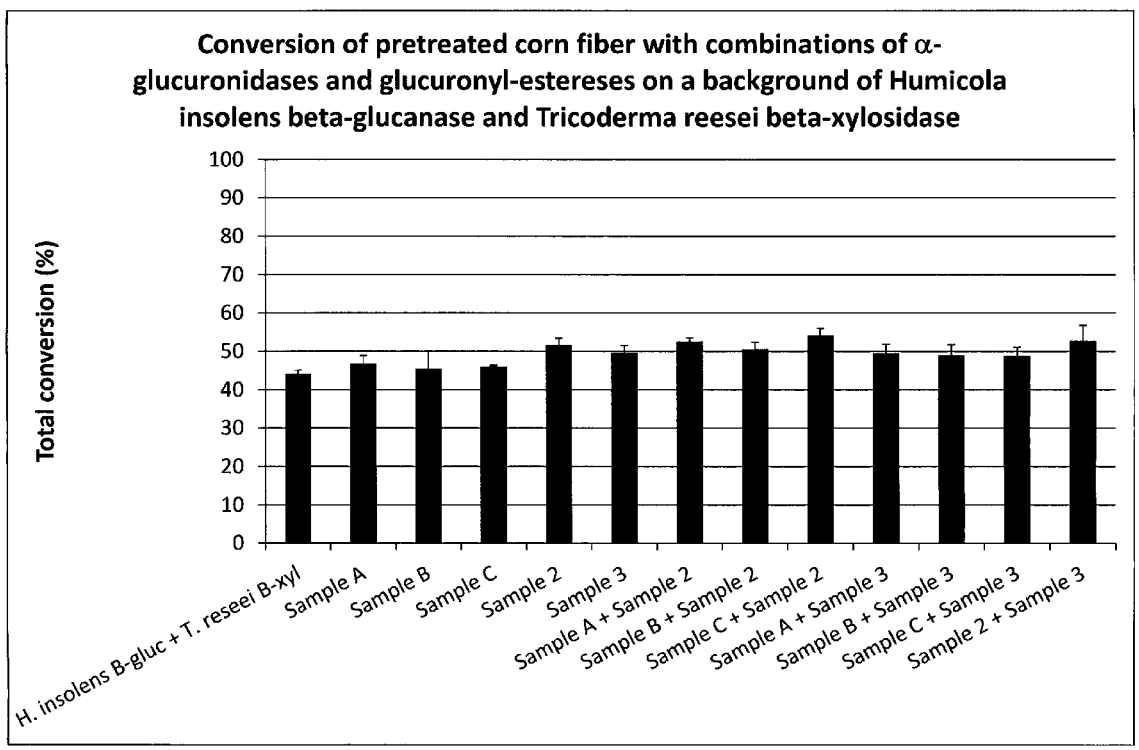
FIG. 3 shows a study of the combined effect of polypeptides having alpha-glucuronidase activity, and polypeptides having glucuronyl esterase activity. Samples; Sample 1: *A. niger* (SEQ ID NO:4); Sample 2: *E. nidulans* (SEQ ID NO:2); Sample 3: *P. aurantiogriseum* (SEQ ID NO:6); Sample 4: *F. johnsoniae* (SEQ ID NO:8),: Sample A, *C. unicolor* (SEQ ID NO:10); Sample B, *T. reesei* (SEQ ID NO:12); Sample C, *C. globosum* (SEQ ID NO:14)

Conversion of Pretreated Corn Fiber after Hydrolysis for 24 Hours with Addition of Glucuronyl-Esterase and Combinations of Glucuronyl-Esterase and Alpha-Glucuronidase As apparent from FIG. 3, addition of alpha-glucuronidase from sample 2 and 3 to hydrolysis mixtures comprising β-glucanase and β-xylosidase enhances the total conversion. Furthermore the combination of the sample 2 alpha-glucuronidase and sample C glucuronyl-esterase increases total conversion even more.

The effect of addition of glucuronyl-esterase and combinations of glucuronyl-esterase and alpha-glucuronidase was evaluated. Corn fiber is a fraction from the wet milling of corn kernels. Corn fiber is the seed coat and residual endosperm left after starch is removed and further processed. Corn fiber was pretreated by autoclaving at 140° C. for 150 minutes. The amount of theoretical arabinose, glucose and xylose in the substrate was determined to be 114, 302, and 204 g per kg dry matter using the following methods.

A mixture of arabinose, galactose, glucose, and xylose (concentration of each component: 0.0050-0.075 g per liter) was used as a standard. Standards of the following concentration were used: 5, 10, 25, 50, 100, 250 and 500 µg/ml were used to determine the concentration of glucuronic acid in the hydrolyzed samples.

The hydrolysis of the pretreated corn fiber was conducted with a *Humicola insolens* beta-glucanase and a *Trichoderma reesei* beta-xylosidase. The *Trichoderma reesei* beta-xylosidase was obtained recombinantly by expression in *Aspergillus oryzae* as described in Rasmussen et al., 2006, *Biotechnology and Bioengineering* 94: 869-876 using standard cultivation methods for *Aspergillus oryzae*.

The hydrolysis of the pretreated corn fiber was performed in 2 ml EPPENDORF® tubes (Eppendorf AG, Germany) at a temperature of 50° C. and a pH of 5.0 in 50 mM succinic acid. Samples were incubated in a THERMOMIXER® Comfort (Eppendorf AG, Germany) that subjected each sample with constant heating and mixing at 1300 rpm. The substrate amount used was 2.5 w/w % in a total sample volume of 2 ml. The alpha-glucuronidases and glucuronyl-esterases were added at an enzyme loading of 1 mg enzyme per g of dry matter on top of both the *Humicola insolens* beta-glucanase and the *Trichoderma reesei* beta-xylosidase. Beta-glucanase was added at a loading of 5 mg enzyme per g of dry matter and the *Trichoderma reesei* beta-xylosidase at a loading of 1 mg enzyme per g of dry matter. Hydrolysis was terminated after 24 hours by heating the samples for 10 minutes at 100° C. in a heat block (Techne Inc., Burlington N.J., USA).

Conversion was calculated by determining the amount of sugars released from the substrate as a percentage of what was added from the start using the formula below but not including initial monomeric sugars. T-tests were performed with a two tailed distribution and equal variance of sample data.

Conversion (%)=(Sugar amount in hydrolysate/Sugar amount in added substr.)×100

Comparing the conversions of pretreated corn fiber when adding glucuronyl-esterases or alpha-glucuronidases or combinations of glucuronyl-esterases and alpha-glucuronidases at an enzyme loading of 1 mg of enzyme per gram dry matter together with 1 mg enzyme per g of dry matter of *Trichoderma reesei* beta-xylosidase and 5 mg enzyme per g of dry matter of Beta-glucanase to just adding 1 mg enzyme per g of dry matter of beta-xylosidase from *Trichoderma reesei* and 5 mg enzyme per g of dry matter of The *Humicola insolens* beta-glucanase demonstrated a significant increases in conversions. Table Y below show the conversion, standard deviation and the t-test significance of all enzymes and combination of enzymes with P 0.05. A superior effect can be observed by addition of 1 mg enzyme per g of dry matter of sample 2 and 1 mg enzyme per g of dry matter of sample C on top of 1 mg enzyme per g of dry matter of beta-xylosidase from *Trichoderma reesei* and 5 mg enzyme per g of dry matter of The *Humicola insolens* beta-glucanase which is significantly higher than adding 1 mg enzyme per g of dry matter of beta-xylosidase from *Trichoderma reesei* and 5 mg enzyme per g of dry matter of The *Humicola insolens* beta-glucanase (P 0.003).

TABLE 3

| Samples | Conversion | Standard deviation | T-test |
|---|---|---|---|
| *Humicola insolens* beta-glucanase and *Trichoderma reesei* beta-xylosidase | 44.1 | 1.0 | Reference |
| *Humicola insolens* beta-glucanase and *Trichoderma reesei* beta-xylosidase and Sample C | 46.1 | 0.3 | 0.032 |
| *Humicola insolens* beta-glucanase and *Trichoderma reesei* beta-xylosidase and Sample 2 | 51.7 | 1.7 | 0.003 |
| *Humicola insolens* beta-glucanase and *Trichoderma reesei* beta-xylosidase and Sample 3 | 49.6 | 2.0 | 0.013 |
| *Humicola insolens* beta-glucanase and *Trichoderma reesei* beta-xylosidase and Sample A and Sample 2 | 52.6 | 0.8 | 0.000 |
| *Humicola insolens* beta-glucanase and *Trichoderma reesei* beta-xylosidase and Sample B and Sample 2 | 50.6 | 1.7 | 0.005 |
| *Humicola insolens* beta-glucanase and *Trichoderma reesei* beta-xylosidase and Sample C and Sample 2 | 54.2 | 1.7 | 0.003 |
| *Humicola insolens* beta-glucanase and *Trichoderma reesei* beta-xylosidase and Sample A and Sample 3 | 49.6 | 2.3 | 0.018 |
| *Humicola insolens* beta-glucanase and *Trichoderma reesei* beta-xylosidase and Sample 2 and Sample 3 | 52.7 | 4.0 | 0.022 |

Aspects

Thus, the invention also relates to the following aspects:

1. An isolated polypeptide having alpha-glucuronidase activity, selected from the group consisting of:
    (a) a polypeptide having at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO:2; or
    at least 95%, at least 96%, at least 97%, at least 98%, at least 99%, or 100% sequence identity to the mature polypeptide of SEQ ID NO:4 or
    at least 95%, at least 96%, at least 97%, at least 98%, at least 99%, or 100% sequence identity to the mature polypeptide of SEQ ID NO:6 or
    at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO:8;
    (b) a polypeptide encoded by a polynucleotide that hybridizes under high stringency conditions, or very high stringency conditions with (i) the mature polypeptide coding sequence of SEQ ID NO:1, (ii) the cDNA sequence thereof, or (iii) the full-length complement of (i) or (ii); or
    or under very high stringency conditions with (iv) the mature polypeptide coding sequence of SEQ ID NO:3, (v) the cDNA sequence thereof, or (vi) the full-length complement of (iv) or (v);
    or under very high stringency conditions with (vii) the mature polypeptide coding sequence of SEQ ID NO:5, (viii) the cDNA sequence thereof, or (ix) the full-length complement of (vii) or (viii);
    or under medium stringency conditions, medium-high stringency conditions, high stringency conditions, or very high stringency conditions with (x) the mature polypeptide coding sequence of SEQ ID NO:7, (xi) the cDNA sequence thereof, or (xii) the full-length complement of (x) or (xi);
    (c) a polypeptide encoded by a polynucleotide having at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:1 or the cDNA sequence thereof or
    having at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:3 or the cDNA sequence thereof or
    having at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:5 or the cDNA sequence thereof or
    having at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:7 or the cDNA sequence thereof.
    (d) a variant of the mature polypeptide of SEQ ID NO:2, SEQ ID NO:4, SEQ ID NO:6 or SEQ ID NO:8 comprising a substitution, deletion, and/or insertion at one or more positions; and (e) a fragment of the polypeptide of (a), (b), (c) or (d) that has alpha-glucuronidase activity.
2. The polypeptide of any of aspects 1, comprising or consisting one of the sequences SEQ ID NO:2, SEQ ID NO:4, SEQ ID NO:6 or SEQ ID NO:8.
3. The polypeptide of any of aspects 1-2, comprising or consisting of the mature polypeptide of one of the sequences SEQ ID NO:2, SEQ ID NO:4, SEQ ID NO:6 or SEQ ID NO:8.
4. The polypeptide of aspect 3, wherein the mature polypeptide is amino acids 23 to 702 of SEQ ID NO:2, 21 to 696 of SEQ ID NO:4, 16 to 690 of SEQ ID NO:6, 33 to 708 of SEQ ID NO:8.
5. The polypeptide of any of aspects 1-4, which is a fragment of SEQ ID NO:2, SEQ ID NO:4, SEQ ID NO:6 or SEQ ID NO:8 wherein the fragment has alpha-glucuronidase activity.
6. A composition comprising the polypeptide of any of aspects 1-5.
7. The composition of aspect 6 further comprising a polypeptide having glucuronyl esterase activity.
8. The composition of aspect 7, wherein the polypeptide having glucuronyl esterase activity, is selected from the group consisting of:
(a) a polypeptide having at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO:10; or
at least 95%, at least 96%, at least 97%, at least 98%, at least 99%, or 100% sequence identity to the mature polypeptide of SEQ ID NO:12 or
at least 95%, at least 96%, at least 97%, at least 98%, at least 99%, or 100% sequence identity to the mature polypeptide of SEQ ID NO:14 or
(b) a polypeptide encoded by a polynucleotide that hybridizes under high stringency conditions, or very high stringency conditions with (i) the mature polypeptide coding sequence of SEQ ID NO:9, (ii) the cDNA sequence thereof, or (iii) the full-length complement of (i) or (ii); or
or under very high stringency conditions with (iv) the mature polypeptide coding sequence of SEQ ID NO:11, (v) the cDNA sequence thereof, or (vi) the full-length complement of (iv) or (v);
or under very high stringency conditions with (vii) the mature polypeptide coding sequence of SEQ ID NO:13, (viii) the cDNA sequence thereof, or (ix) the full-length complement of (vii) or (viii);
(c) a polypeptide encoded by a polynucleotide having at least 80%, at least 85%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:9 or the cDNA sequence thereof or
having at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:11 or the cDNA sequence thereof or
having at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO:13 or the cDNA sequence thereof or (d) a variant of the mature polypeptide of SEQ ID NO:10, SEQ ID NO:12 or SEQ ID NO:14 comprising a substitution, deletion, and/or insertion at one or more positions; and
(e) a fragment of the polypeptide of (a), (b), (c) or (d) that has glucuronyl esterase activity.
9. The composition of aspect 7 or 8 wherein the polypeptide having glucuronyl esterase activity comprises or consists of one of the sequences SEQ ID NO:10, SEQ ID NO:12 or SEQ ID NO:14.
10. The composition of any of aspects 7 to 9 wherein the polypeptide having glucuronyl esterase activity comprise or consists consisting of the mature polypeptide of one of the sequences SEQ ID NO:10, SEQ ID NO:12 or SEQ ID NO:14.
11. The composition of aspect 10, wherein the mature polypeptide is amino acids 101 to 474 of SEQ ID NO:10, 94 to 460 of SEQ ID NO:12 or 21 to 392 of SEQ ID NO:14.
12. The composition of any of aspects 7 to 11 wherein the polypeptide having glucuronyl esterase activity is a fragment of SEQ ID NO:10, SEQ ID NO:12 or SEQ ID NO:14 wherein the fragment has glucuronyl esterase activity.
13. An isolated polynucleotide encoding the polypeptide of any of aspects 1-5.
14. A nucleic acid construct or expression vector comprising the polynucleotide of aspect 13 operably linked to one or more control sequences that direct the production of the polypeptide in an expression host.
15. A recombinant host cell comprising the polynucleotide of aspect 13 operably linked to one or more control sequences that direct the production of the polypeptide.
16. A method of producing the polypeptide of any of aspects 1-5, comprising:
(a) cultivating a cell, which in its wild-type form produces the polypeptide, under conditions conducive for production of the polypeptide; and
(b) recovering the polypeptide.
17. A method of producing a polypeptide having alpha-glucuronidase activity, comprising:
(a) cultivating the host cell of aspect 15 under conditions conducive for production of the polypeptide; and
(b) recovering the polypeptide.
18. A transgenic plant, plant part or plant cell transformed with a polynucleotide encoding the polypeptide of any of aspects 1-5.
19. A method of producing a polypeptide having alpha-glucuronidase activity, comprising:
(a) cultivating the transgenic plant or plant cell of aspect 18 under conditions conducive for production of the polypeptide; and
(b) recovering the polypeptide.
20. A method of producing a mutant of a parent cell, comprising inactivating a polynucleotide encoding the polypeptide of any of aspects 1-5, which results in the mutant producing less of the polypeptide than the parent cell.
21. A mutant cell produced by the method of aspect 20.
22. The mutant cell of aspect 21, further comprising a gene encoding a native or heterologous protein.
23. A method of producing a protein, comprising:
(a) cultivating the mutant cell of aspect 21 or 22 under conditions conducive for production of the protein; and
(b) recovering the protein.

24. A double-stranded inhibitory RNA (dsRNA) molecule comprising a subsequence of the polynucleotide of aspect 13, wherein optionally the dsRNA is a siRNA or a miRNA molecule.
25. The double-stranded inhibitory RNA (dsRNA) molecule of aspect 24, which is about 15, 16, 17, 18, 19, 20, 21, 22, 23, 24, 25 or more duplex nucleotides in length.
26. A method of inhibiting the expression of a polypeptide having alpha-glucuronidase activity in a cell, comprising administering to the cell or expressing in the cell the double-stranded inhibitory RNA (dsRNA) molecule of aspect 24 or 25.
27. The method of aspect 26, wherein the dsRNA is about 15, 16, 17, 18, 19, 20, 21, 22, 23, 24, or more duplex nucleotides in length.
28. A cell produced by the method of aspect 26 or 27.
29. The cell of aspect 28, further comprising a gene encoding a native or heterologous protein.
30. A method of producing a protein, comprising:
    (a) cultivating the cell of aspect 28 or 29 under conditions conducive for production of the protein; and
    (b) recovering the protein.
31. An isolated polynucleotide encoding a signal peptide comprising or consisting of amino acids 1 to 22 of SEQ ID NO:2 or amino acids 1 to 20 of SEQ ID NO:4 or amino acids 1 to 15 of SEQ ID NO:6 or amino acids 1 to 27 of SEQ ID NO:8.
32. A nucleic acid construct or expression vector comprising a gene encoding a protein operably linked to the polynucleotide of aspect 31, wherein the gene is foreign to the polynucleotide encoding the signal peptide.
33. A recombinant host cell comprising a gene encoding a protein operably linked to the polynucleotide of aspect 31, wherein the gene is foreign to the polynucleotide encoding the signal peptide.
34. A method of producing a protein, comprising:
    (a) cultivating a recombinant host cell comprising a gene encoding a protein operably linked to the polynucleotide of aspect 31, wherein the gene is foreign to the polynucleotide encoding the signal peptide, under conditions conducive for production of the protein; and
    (b) recovering the protein.
35. A method for degrading or converting a cellulosic material, comprising: treating the cellulosic material with an enzyme composition in the presence of the polypeptide having alpha-glucuronidase activity of any of aspects 1-5.
36. A method for degrading or converting a cellulosic material, comprising: treating the cellulosic material with an enzyme composition of any of aspects 6 to 12.
37. The method of aspect 35 or 36, wherein the cellulosic material is pretreated.
38. The method of any of aspects 35 to 37, wherein the enzyme composition comprises one or more enzymes selected from the group consisting of a cellulase, a polypeptide having cellulolytic enhancing activity, a hemicellulase, an esterase, a protease, a laccase, or a peroxidase.
39. The method of aspect 38, wherein the cellulase is one or more enzymes selected from the group consisting of an endoglucanase, a cellobiohydrolase, and a beta-glucosidase.
40. The method of aspect 38, wherein the hemicellulase is one or more enzymes selected from the group consisting of a xylanase, an acetyxylan esterase, a feruloyl esterase, an arabinofuranosidase, a xylosidase, and a glucuronidase.
41. The method of any of aspects 35-40, further comprising recovering the degraded cellulosic material.
42. The method of aspect 41, wherein the degraded cellulosic material is a sugar.
43. The method of aspect 42, wherein the sugar is selected from the group consisting of glucose, xylose, mannose, galactose, and arabinose.
44. A method for producing a fermentation product, comprising:
    (a) saccharifying a cellulosic material with an enzyme composition in the presence of the polypeptide having alpha-glucuronidase activity of any of aspects 1-5;
    (b) fermenting the saccharified cellulosic material with one or more fermenting microorganisms to produce the fermentation product; and
    (c) recovering the fermentation product from the fermentation.
45. A method for producing a fermentation product, comprising:
    (a) saccharifying a cellulosic material with an enzyme composition of any of aspects 6-12
    (b) fermenting the saccharified cellulosic material with one or more fermenting microorganisms to produce the fermentation product; and
    (c) recovering the fermentation product from the fermentation.
46. The method of aspect 44 or 45, wherein the cellulosic material is pretreated.
47. The method of any of aspects 44 to 46, wherein the enzyme composition comprises one or more enzymes selected from the group consisting of a cellulase, a polypeptide having cellulolytic enhancing activity, a hemicellulase, an esterase, a protease, a laccase, or a peroxidase.
48. The method of aspect 47, wherein the cellulase is one or more enzymes selected from the group consisting of an endoglucanase, a cellobiohydrolase, and a beta-glucosidase.
49. The method of aspect 47, wherein the hemicellulase is one or more enzymes selected from the group consisting of a xylanase, an acetyxylan esterase, a feruloyl esterase, an arabinofuranosidase, a xylosidase, and a glucuronidase.
50. The method of any of aspects 44-49, wherein steps (a) and (b) are performed simultaneously in a simultaneous saccharification and fermentation.
51. The method of any of aspects 44-50, wherein the fermentation product is an alcohol, an organic acid, a ketone, an amino acid, or a gas.
52. A method of fermenting a cellulosic material, comprising: fermenting the cellulosic material with one or more fermenting microorganisms, wherein the cellulosic material is saccharified with an enzyme composition in the presence of a polypeptide having alpha-glucuronidase activity of any of aspects 1-5.
53. A method of fermenting a cellulosic material, comprising: fermenting the cellulosic material with one or more fermenting microorganisms, wherein the cellulosic material is saccharified with an enzyme composition of any of aspects 6 to 12.
54. The method of aspect 52 or 53, wherein the fermenting of the cellulosic material produces a fermentation product.

55. The method of any of aspects 52 to 54, further comprising recovering the fermentation product from the fermentation.
56. The method of any of aspects 52 to 55, wherein the cellulosic material is pretreated before saccharification.
57. The method of any of aspects 52 to 56, wherein the enzyme composition comprises one or more enzymes selected from the group consisting of a cellulase, a polypeptide having cellulolytic enhancing activity, a hemicellulase, an esterase, a protease, a laccase, or a peroxidase.
58. The method of aspect 57, wherein the cellulase is one or more enzymes selected from the group consisting of an endoglucanase, a cellobiohydrolase, and a beta-glucosidase.
59. The method of aspect 57, wherein the hemicellulase is one or more enzymes selected from the group consisting of a xylanase, an acetyxylan esterase, a feruloyl esterase, an arabinofuranosidase, a xylosidase, and a glucuronidase.
60. The method of any of aspects 52 to 59, wherein the fermentation product is an alcohol, an organic acid, a ketone, an amino acid, or a gas.

The invention claimed is:

1. A nucleic acid construct comprising a polynucleotide encoding a polypeptide having alpha-qlucuronidase activity, wherein the polynucleotide is operably linked to one or more heterologous control sequences that direct the production of the polypeptide in an expression host, and wherein the polypeptide having alpha-qlucuronidase activity is selected from the group consisting of:
   (a) a polypeptide having at least 80% sequence identity to the mature polypeptide of SEQ ID NO: 2;
   (b) a polypeptide encoded by a polynucleotide that hybridizes under high stringency conditions with (i) the mature polypeptide coding sequence of SEQ ID NO:1, (ii) the cDNA sequence thereof, or (iii) the full-length complement of (i) or (ii), wherein high stringency conditions are defined as prehybridization and hybridization at 42° C. in 5× SSPE, 0.3% SDS, 200 micrograms/ml sheared and denatured salmon sperm DNA, and 50% formamide, and washing three times each for 15 minutes using 2× SSC, 0.2% SDS at 65° C.; and
   (c) a polypeptide encoded by a polynucleotide having at least 80% sequence identity to the mature polypeptide coding sequence of SEQ ID NO:1 or the cDNA sequence thereof.

2. An isolated recombinant host cell transformed with the nucleic acid construct of claim 1 operably linked to one or more control sequences that direct the production of the polypeptide.

3. A method of producing a polypeptide having alpha-glucuronidase activity, comprising:
   (a) cultivating the recombinant host cell of claim 2 under conditions conducive for production of the polypeptide; and
   (b) recovering the polypeptide.

4. The nucleic acid construct of claim 1, wherein the polypeptide has at least 80% sequence identity to the mature polypeptide of SEQ ID NO: 2.

5. The nucleic acid construct of claim 1, wherein the polypeptide has at least 85% sequence identity to the mature polypeptide of SEQ ID NO: 2.

6. The nucleic acid construct of claim 1, wherein the polypeptide has at least 90% sequence identity to the mature polypeptide of SEQ ID NO: 2.

7. The nucleic acid construct of claim 1, wherein the polypeptide has at least 95% sequence identity to the mature polypeptide of SEQ ID NO: 2.

8. The nucleic acid construct of claim 1, wherein the polypeptide comprises SEQ ID NO: 2.

9. The nucleic acid construct of claim 1, wherein the polypeptide consists of SEQ ID NO: 2.

10. The nucleic acid construct of claim 1, wherein the polypeptide comprises the mature polypeptide of SEQ ID NO: 2.

11. The nucleic acid construct of claim 1, wherein the polypeptide consists of the mature polypeptide of SEQ ID NO: 2.

12. The nucleic acid construct of claim 1, wherein the mature polypeptide is amino acids 23 to 702 of SEQ ID NO: 2.

13. The nucleic acid construct of claim 1, wherein the polypeptide is encoded by a polynucleotide that hybridizes under high stringency conditions with (i) the mature polypeptide coding sequence of SEQ ID NO:1, (ii) the cDNA sequence thereof, or (iii) the full-length complement of (i) or (ii), wherein high stringency conditions are defined as prehybridization and hybridization at 42° C. in 5× SSPE, 0.3% SDS, 200 micrograms/ml sheared and denatured salmon sperm DNA, and 50% formamide, and washing three times each for 15 minutes using 2× SSC, 0.2% SDS at 65° C.

14. The nucleic acid construct of claim 1, wherein the polypeptide is encoded by a polynucleotide that hybridizes under very high stringency conditions with (i) the mature polypeptide coding sequence of SEQ ID NO:1, (ii) the cDNA sequence thereof, or (iii) the full-length complement of (i) or (ii), wherein very high stringency conditions are defined as prehybridization and hybridization at 42° C. in 5× SSPE, 0.3% SDS, 200micrograms/ml sheared and denatured salmon sperm DNA, and 50% formamide, and washing three times each for 15 minutes using 2× SSC, 0.2% SDS at 70° C.

15. The nucleic acid construct of claim 1, wherein the polypeptide is encoded by a polynucleotide having at least 80% sequence identity to the mature polypeptide coding sequence of SEQ ID NO:1 or the cDNA sequence thereof.

16. The nucleic acid construct of claim 1, wherein the polypeptide is encoded by a polynucleotide having at least 85% sequence identity to the mature polypeptide coding sequence of SEQ ID NO:1 or the cDNA sequence thereof.

17. The nucleic acid construct of claim 1, wherein the polypeptide is encoded by a polynucleotide having at least 90% sequence identity to the mature polypeptide coding sequence of SEQ ID NO:1 or the cDNA sequence thereof.

18. The nucleic acid construct of claim 1, wherein the polypeptide is encoded by a polynucleotide having at least 95% sequence identity to the mature polypeptide coding sequence of SEQ ID NO:1 or the cDNA sequence thereof.

19. The nucleic acid construct of claim 1, wherein the mature polypeptide coding sequence is nucleotides 1 to 2544 of SEQ ID NO: 1.

20. The nucleic acid construct of claim 1, wherein the polypeptide is a fragment of the mature polypeptide of SEQ ID NO: 2, which has alpha-glucuronidase activity.

21. An expression vector comprising the nucleic acid construct of claim 1.

22. The nucleic acid construct of claim 1, wherein the polypeptide has at least 91% sequence identity to the mature polypeptide of SEQ ID NO: 2.

23. The nucleic acid construct of claim 1, wherein the polypeptide has at least 92% sequence identity to the mature polypeptide of SEQ ID NO: 2.

24. The nucleic acid construct of claim 1, wherein the polypeptide has at least 93% sequence identity to the mature polypeptide of SEQ ID NO: 2.

25. The nucleic acid construct of claim 1, wherein the polypeptide has at least 94% sequence identity to the mature polypeptide of SEQ ID NO: 2.

26. The nucleic acid construct of claim 1, wherein the polypeptide has at least 96% sequence identity to the mature polypeptide of SEQ ID NO: 2.

27. The nucleic acid construct of claim 1, wherein the polypeptide has at least 97% sequence identity to the mature polypeptide of SEQ ID NO: 2.

28. The nucleic acid construct of claim 1, wherein the polypeptide has at least 98% sequence identity to the mature polypeptide of SEQ ID NO: 2.

29. The nucleic acid construct of claim 1, wherein the polypeptide has at least 99% sequence identity to the mature polypeptide of SEQ ID NO: 2.

* * * * *

UNITED STATES PATENT AND TRADEMARK OFFICE
CERTIFICATE OF CORRECTION

PATENT NO. : 9,446,102 B2
APPLICATION NO. : 14/395960
DATED : September 20, 2016
INVENTOR(S) : Johan Börjesson It is certified that error appears in the above-identified patent and that said Letters Patent is hereby corrected as shown below:

At Column 1, Line 3 please insert the following information:
--Statement as to Rights to Inventions Made Under Federally Sponsored Research and Development
This invention was made with Government support under Cooperative Agreement DE-FC36-08GO18080 awarded by the Department of Energy. The government has certain rights in this invention.--

Signed and Sealed this
Fifth Day of February, 2019

Andrei Iancu
*Director of the United States Patent and Trademark Office*